United States Patent [19]
Struble et al.

[11] Patent Number: 6,122,545
[45] Date of Patent: Sep. 19, 2000

[54] MULTIPLE CHANNEL SEQUENTIAL CARDIAC PACING METHOD

[75] Inventors: Chester L. Struble, Eijsden; Cobus De Roos, Landgraat; Albert-Jan Nijsten, Beek, all of Netherlands

[73] Assignee: Medtronic, Inc., Minneapolis, Minn.

[21] Appl. No.: 09/067,729

[22] Filed: Apr. 28, 1998

[51] Int. Cl.⁷ .................................................. A61N 1/368
[52] U.S. Cl. ........................................................... 607/9
[58] Field of Search ...................................... 607/4, 9, 14

[56] References Cited

U.S. PATENT DOCUMENTS

| | | |
|---|---|---|
| 3,937,226 | 2/1976 | Funke . |
| 4,088,140 | 5/1978 | Rockland et al. . |
| 4,332,259 | 6/1982 | McCorkle, Jr. . |
| 4,354,497 | 10/1982 | Kahn . |
| 4,458,677 | 7/1984 | McCorkle, Jr. . |
| 4,548,203 | 10/1985 | Tacker, Jr. et al. . |
| 4,928,688 | 5/1990 | Mower . |
| 5,085,213 | 2/1992 | Cohen ......................................... 607/4 |
| 5,156,149 | 10/1992 | Hudrlik . |
| 5,174,289 | 12/1992 | Cohen . |
| 5,233,985 | 8/1993 | Hudrlik . |
| 5,267,560 | 12/1993 | Cohen . |
| 5,370,665 | 12/1994 | Hudrlik . |
| 5,514,161 | 5/1996 | Limousin . |
| 5,584,867 | 12/1996 | Limousin et al. . |
| 5,674,259 | 10/1997 | Gray . |
| 5,800,465 | 9/1998 | Thompson et al. .......................... 607/9 |
| 5,814,079 | 9/1998 | Kieval ......................................... 607/9 |

OTHER PUBLICATIONS

Daubert et al., "Permanent Dual Atrium Pacing in Major Intratrial Conduction Blocks: A Four Years Experience", *PACE*, vol. 16, Part II, NASPE Abstract 141, p. 885, Apr. 1993.

Daubert et al., "Outcome of Patients Chronically Implanted With Biventricular Pacing Systems for End Stage Congestive Heart Failure", *PACE*, vol. 20, Part II, NASPE Abstract 215, Apr., 1997.

Daubert et al., "Use of Specifically Designed Coronary Sinus Leads for Permanent Left Ventricular Pacing: Preliminary Experience", *PACE,* vol. 20, Part II, NASPE Abstract 17, Apr., 1997.

Leclercq et al., "Acute Hemodynamic Response to Biventricular DDD Pacing in Patients with Severe Congestive Heart Failure and Without Conventional Indication for Permanent Pacemaker", *Abstracts From the 70th Scientific Sessions,* I–95, Abstract 520, Oct. 21, 1997.

(List continued on next page.)

*Primary Examiner*—William E. Kamm
*Attorney, Agent, or Firm*—Thomas F. Woods; Harold R. Patton

[57] ABSTRACT

Multi-chamber cardiac pacing systems for providing synchronous pacing to at least the two upper heart chambers or the two lower heart chambers or to three heart chambers or to all four heart chambers employing programmable conduction delay window (CDW) times timed out from paced and sensed events occurring in each heart chamber are disclosed. The synchronous pacing of one of the right and left heart chambers is provided on demand following expiration of programmable pace and sense CDWs that are started by both a paced event and a sensed event first occurring in the other of the right and left heart chambers. The delivery of the pacing pulse is inhibited by a sensed event detected in the other of the right and left heart chambers before the expiration of the corresponding CDW. In a four channel atrial and ventricular pacing system, the right and left atrial chambers are sensed and paced as necessary upon at the end of a V-A escape interval and right and left AV delays are commenced for sensing ventricular depolarizations in the right and left ventricles. The four channel system is programmable to pace and sense in three selected heart chambers.

32 Claims, 8 Drawing Sheets

OTHER PUBLICATIONS

Daubert et al., "Permanent Left Ventricular Pacing With Transvenous Leads Inserted Into The Coronary Veins", *PACE* (vol. 21, Part II, pp. 239–245, Jan. 1998).

Cazeau et al., "Four Chamber Pacing in Dilated Cardiomyopathy", *PACE* (vol. 17, Part II, PP. 1974–1979, Nov. 1994).

Daubert et al., "Renewal of Permanent Left Atrial Pacing via the Coronary Sinus", *PACE* (vol. 15, Part II, NASPE Abstract 255, p. 572, Apr. 1992).

Durrer et al., "Total Excitation of the Isolated Human Heart", *Circulation* (vol. XLI, pp. 899–912, Jun. 1970).

Daubert et al, "Simultaneous Dual Atrium Pacing in High Degree Interatrial Blocks: Hemodynamic Results" AHA 1991, Abstract from 64th Scientific Sessions, # 1804.

Mabo et al., "Prevention of Atrial Tachyarrhythmias Related to Advanced Interatrial Block by Permanent Atrial Resynchronization", *PACE,* vol. 14, Apr. 1991, Part II, p. 648, Abstract 122.

Daubert et al., "Hemodynamic Benefits of Permanent Atrial Resynchronization in Patients with Advanced Interatrial Blocks, Paced in DDD Mode", *PACE,* vol. 14, Apr. 1991, Part II, p. 650, # 130.

MULTIPLE CHANNEL SEQUENTIAL CARDIAC PACING METHOD

CROSS-REFERENCE TO RELATED APPLICATIONS

Reference is hereby made to commonly assigned U.S. patent application Ser. No. 09/067,751 filed on even date herewith, now U.S. Pat. No. 5,902,324, for BI-ATRIAL AND/OR BI-VENTRICULAR, SEQUENTIAL CARDIAC PACING SYSTEMS filed in the names of D. Thompson et al.

FIELD OF THE INVENTION

The present invention pertains to multi-chamber cardiac pacing systems for providing synchronous pacing to at least the two upper heart chambers or the two lower heart chambers or to three heart chambers or to all four heart chambers employing programmable conduction delay window (CDW) times timed out from paced and sensed events occurring in each heart chamber.

BACKGROUND OF THE INVENTION

The cardiovascular system provides oxygenated blood to various structures of the body. In a normally functioning heart, the body's demand for oxygenated blood varies, and the heart responds by increasing or decreasing its rate and force of contraction to meet the demand. An electrical signal generated by the sinus node in the upper right atrial wall near the base of the heart is conducted through the upper heart chambers, i.e., the right and left atria, and causes them to contract in a synchronous manner. The contraction of the upper heart chambers forces blood pooled therein through open heart valves and into the right and left ventricles or lower heart chambers. The atrial electrical depolarization wave arrives at the AV node superior to the ventricles and triggers the conduction of a ventricular depolarization wave down the bundle of His in the septum between the right and left ventricles to the apex of the heart. The ventricles contract after a brief atrio-ventricular (AV) delay time following the sinus node depolarization as the depolarization wave then advances superiorly, posteriorly, and anteriorly throughout the outer ventricular wall of the heart. The lower heart chambers contract and force the blood through the vascular system of the body. The contraction of the right and left ventricles proceeds in an organized fashion which optimizes emptying of the ventricular chambers. The synchronous electrical depolarization of the atrial and ventricular chambers can be electrically sensed and displayed, and the electrical waveform is characterized by accepted convention as the "PQRST" complex. The PQRST complex includes the P-wave, corresponding to the atrial depolarization wave, the R-wave, corresponding to the ventricular depolarization wave, and the T-wave which represents the re-polarization of the cardiac cells.

Various disease mechanisms cause conduction disturbances which interfere with the natural conduction system of the heart and affect the heart's ability to provide adequate cardiac output to the body. In certain disease mechanisms, the sinus node fails to depolarize and commence the P-wave as rapidly as required to satisfy the demand for oxygenated blood, or the atria may spontaneously depolarize at rates that are well in excess of the ability of the ventricles to respond. In these situations, the ventricles may compensate by depolarizing spontaneously from ectopic depolarization sites. In other cases where the SA node operates correctly, 1:1 atrial and ventricular depolarization synchrony is lost because the AV node fails to respond to all P-waves or a defect in the bundle of His interferes with the conduction of the ventricular depolarization. In all of these cases, the ventricles may contract at an inadequate rate to provide adequate cardiac output.

When the atria or ventricles contract too slowly, the patient may be a candidate for implantation with a cardiac pacemaker for restoring the heart rate by applying pacing pulses to the heart chamber that is malfunctioning at a pacing rate that restores adequate cardiac output. Modern implantable cardiac pacemakers comprise an implantable pulse generator (IPG) and a lead or leads extending from the IPG to pace/sense electrode or electrodes located with respect to the heart chamber to deliver the pacing pulses and sense the P-wave or R-wave. Typically, the leads are transvenously introduced into the particular heart chamber via the superior vena cava and right atrium, and the pace/sense electrodes are maintained in contact with the heart tissue by a fixation mechanism at the distal end of the lead. However, leads may be placed subcutaneously between the IPG and the exterior of the heart, and the pace/sense electrodes attached to the epicardium at the desired sites. Moreover, endocardial coronary sinus leads are introduced through the right atrium into the coronary sinus and the great vein to locate pace/sense electrodes in proximity to the left atrium or the left ventricle.

A single chamber, demand pacemaker is implanted to supply pacing pulses to a single upper or lower heart chamber, typically the right atrium or right ventricle, in response to bradycardia of the same chamber. In an atrial, demand pacemaker operating in the AAI pacing mode, an atrial pacing pulse is delivered to the atrial pace/sense electrodes by the IPG if a P-wave is not sensed by an atrial sense amplifier coupled to the atrial pace/sense electrodes within an atrial escape interval (A—A interval) timed by an atrial escape interval timer. In a ventricular, demand pacemaker operating in the VVI pacing mode, a ventricular pacing pulse to the ventricular pace/sense electrodes if an R-wave is not sensed by a ventricular sense amplifier coupled to the ventricular pace/sense electrodes within a ventricular escape interval (V—V interval) timed by a ventricular escape interval timer.

A dual chamber, demand pacemaker is implanted to supply pacing pulses when required to one upper heart chamber and to one lower heart chamber, typically the right atrium and right ventricle. In a dual chamber, demand pacemaker operating in the DDD pacing mode, both the AAI and VVI pacing modes are followed under the above defined conditions. A ventricular pacing pulse is delivered to the ventricular pace/sense electrodes if an R-wave is not sensed by the ventricular sense amplifier coupled thereto within an AV time interval timed from the sensing of a P-wave by the atrial sense amplifier.

Over the years, it has been proposed that various conduction disturbances involving both bradycardia and tachycardia of a heart chamber could benefit from stimulation applied at multiple electrode sites positioned in or about it in synchrony with a depolarization which has been sensed at least one of the electrode sites. In addition, it has been proposed to employ pacing to compensate for conduction defects and in congestive heart failure where depolarizations that naturally occur in one upper or lower chamber are not conducted quickly enough to the other upper or lower heart chamber. In such cases, the right and left heart chambers do not contract in optimum synchrony with each other, and cardiac output suffers due to the timing imbalance. In other cases, spontaneous depolarizations of the left atrium or left ventricle occur at ectopic foci in these left heart chambers, and the natural activation sequence is grossly disturbed. In such cases, cardiac output deteriorates because the contractions of the right and left heart chambers are not synchronized sufficiently to eject blood therefrom.

In patients suffering from congestive heart failure, the hearts become dilated, and the conduction and depolarization sequences of the heart chambers may exhibit Intra-Atrial Conduction Defects (IACD), Left Bundle Branch Block (LBBB), Right Bundle Branch Block (RBBB), and Intra Ventricular Conduction Defects (IVCD). Single and dual chamber pacing of the right atrium and/or right ventricle can be counterproductive in such cases, depending on the defective conduction pathway and the locations of the pace/sense electrodes.

A number of proposals have been advanced for providing pacing therapies to alleviate these conditions and restore synchronous depolarization of right and left, upper and lower, heart chambers . The proposals appearing in U.S. Pat. Nos. 3,937,266, 4,088,140, 4,548,203, 4,458,677, 4,332,259 are summarized in U.S. Pat. Nos. 4,928,688 and 5,674,259, all incorporated herein by reference. The advantages of providing sensing at pace/sense electrodes located in both the right and left heart chambers is addressed in the '688 and '259 patents, as well as in U.S. Pat. Nos. 4,354,497, 5,174, 289, 5,267,560, 5,514,161, and 5,584,867, also incorporated herein by reference. Typically, the right atrium is paced at expiration of an A—A escape interval, and the left atrium is simultaneously paced or synchronously paced after a short delay time. Similarly, the right ventricle is paced at expiration of a V—V escape interval, and the left ventricle is simultaneously paced or synchronously paced after a short delay time. Some of these patents propose limited forms of DDD pacing having "bi-ventricular" or "bi-atrial" demand or triggered pacing functions. In all cases, a pacing pulse delivered at the end of an escape interval or at the end of an AV delay (a "paced event") triggers the simultaneous or slightly delayed delivery of the pacing pulse to the other heart chamber. They do not propose pacing a right or left heart chamber at the end of the escape interval or AV delay and then inhibiting pacing in the other of the right or left heart chamber if a conducted depolarization is detected in that other heart chamber within a physiologic time related to the location of the pace/sense electrodes.

In the above-incorporated '259 patent, a combined epicardial IPG and electrode array are proposed for fitting about the apical region of the heart and providing a VVI pacing function providing for substantially simultaneous depolarization of both ventricles through selected ones of the pace/sense electrodes on time out of a V—V escape interval. It is not clear what occurs if an R-wave is sensed at one of the left or right ventricular pace/sense electrodes within the V—V escape interval.

In the '688 patent, two or three chamber pacing systems are disclosed wherein a programmable synchronization time window of about 5–10 msec duration is started on sensing an R-wave or a P-wave at pace/sense electrodes in one of the ventricles or atria before the expiration of a V—V or an A—A escape interval, respectively. The delivery of the pacing pulse in the other atrium or ventricle is inhibited if a P-wave or an R-wave is sensed at the pace/sense electrode site in that chamber within the synchronization time window. Atrial or ventricular pacing pulses are delivered simultaneously to both left and right atrial or ventricular pace/sense electrodes, if the V—V escape interval times out without sensing a P-wave or an R-wave at either pace/sense electrode site. In a DDD pacemaker context, an atrial pace/sense electrode, sense amplifier and pace output circuit and a pair of ventricular pace/sense electrodes, sense amplifiers and pace output circuits are provided. The AV delay timer is started when a P-wave is sensed, and ventricular pacing pulses are preferably supplied simultaneously to the two ventricular pace/sense electrodes if an R-wave is not sensed by either ventricular sense amplifier before the AV delay times out.

A "double atrial, triple chamber" pacing system is described in the '161 and '867 patents for treating dysfunctional atrial conduction using a programmable DDD pacemaker for pacing both atria simultaneously when an atrial sensed event is detected from either chamber or at the expiration of a V-A escape interval. The IPG includes atrial sense amplifiers coupled to atrial pace/sense electrodes positioned with respect to electrode sites in or adjacent the right and left atria and a ventricular sense amplifier coupled to ventricular pace/sense electrodes located in or on the right ventricle. In the '161 patent, ventricular pacing pulses are applied to the ventricular pace/sense electrodes at the end of an AV delay timed from the atrial paced events unless the sensed atrial rate exceeds a rate limit. In the '867 patent, a fall back mode is commenced to limit the ventricular pacing rate if the sensed P-waves are deemed "premature". Clinical experience in use of double atrial, three chamber, pacing systems appears in abstracts by Daubert et al., including "Permanent Dual Atrium Pacing in Major Intratrial Conduction Blocks: A Four Years Experience" appearing in *PACE* (Vol. 16, Part II, NASPE Abstract 141, p.885, April 1993). In these systems, atrial pacing pulses are delivered simultaneously in a triggered mode to both atria that is wasteful of electrical energy and fails to maintain a physiologic delay between the evoked depolarizations of the atria.

Further clinical experience with two, three and four heart chamber pacing is also reported by Daubert et al. in "Permanent Left Ventricular Pacing With Transvenous Leads Inserted Into The Coronary Veins" appearing in *PACE* (Vol. 21, Part II, pp. 239–245, January 1998). In the two heart chamber context, Daubert et al. report implanting conventional DDDR IPGs with the atrial pace/sense terminals coupled to a left ventricular lead having pace/sense electrodes located in relation to the left ventricle. The ventricular pace/sense terminals were coupled to right ventricular leads having pace/sense electrodes located in relation to the right ventricle. The IPG was programmed to operate in the VVIR mode with short AV delays, e.g. 30 ms, for timing delivery of a pacing pulse to the right ventricle when an R-wave was first sensed in or a pacing pulse was delivered to the left ventricle at the end of the programmed V-A escape interval. In this bi-ventricular pacing system, ventricular pacing pulses were not delivered in a triggered mode to both ventricles, but only the conduction delay from the left ventricle to the right ventricle could be programmed.

Daubert et al. also report use of a "double ventricular, triple chamber" pacing system in this article using DDDR IPGs having the atrial terminals coupled with the atrial pacing lead and the ventricular terminals coupled through an adaptor to two ventricular pacing leads. The pace/sense electrodes of the atrial pacing lead were implanted apparently in relation to the right atrium and the pace/sense electrodes of the ventricular pacing leads were implanted in relation to the right and left ventricles. The DDDR IPG was programmed in the DDDR mode to provide simultaneous pacing of the right and left ventricles at the end of an A-V delay timed from an atrial paced event at the expiration of the V-A pacing escape interval or an atrial sensed event occurring during the V-A escape interval. In this system, the simultaneous delivery of ventricular pacing pulses to both ventricles is wasteful of electrical energy and fails to maintain a physiologic delay between the evoked depolarizations of the ventricles.

A four chamber DDD pacing system providing right and left chamber pacing and sensing is described in this Daubert et al, article and in an article by Cazeau et al. entitled "Four Chamber Pacing in Dilated Cardiomyopathy" appearing in *PACE* (Vol. 17, Part II, pp. 1974–1979, November 1994). In these four chamber systems, right and left atrial leads are coupled "in series" through a bifurcated bipolar adaptor with atrial pace/sense connector block terminals, and right and left ventricular leads are coupled "in series" through a bifurcated bipolar adaptor with ventricular pace/sense connector block terminals. Right atrial and right ventricular leads are connected to the cathode ports, while left atrial and left ventricular leads are connected to the anode ports of each bipolar bifurcated adaptor. The IPG is programmed in the DDD mode and in a bipolar pacing mode with a common AV delay that is commenced by the delivery of atrial pacing pulses. The earliest right or left atrial sensed event (i.e., P-wave) within a V-A escape interval or the expiration of the V-A escape interval triggers delivery of atrial pacing pulses to both of the pace/sense electrodes in both atrial chambers through the series connected, right and left atrial leads. It appears that the sensing "in series" of either a right or left ventricular R-wave across the right and left pace/sense electrode pair during the AV delay terminates the AV delay and triggers delivery of ventricular pace pulses across the right and left pace/sense electrode pair. In this pacing system, both atrial and ventricular pacing pulses are delivered to both atria and both ventricles on sensing a P-wave and on sensing an R-wave, respectively, which is wasteful of electrical energy. And, the resulting simultaneous depolarization of the right and left atria or the right and left ventricles is not physiologically beneficial in many instances.

In these approaches, the atrial and/or ventricular pace/sense electrodes are located in a variety of locations and manner with respect to the right and left atria and/or right and left ventricles. In the '688 patent, one ventricular pace/sense electrode is located at the distal end of an endocardial lead introduced deeply into the great vein extending from the coronary sinus to place it adjacent to the left ventricle. It is also known that the pace/sense electrode of an endocardial lead can be placed closer to the entrance to the coronary sinus and adjacent the left atrium. Such an approach is shown in the above-referenced Cazeau et al. article and in an abstract by Daubert et al., "Renewal of Permanent Left Atrial Pacing via the Coronary Sinus", appearing in *PACE* (Vol. 15, Part II, NASPE Abstract 255, p. 572, April 1992), incorporated herein by reference. Epicardial screw-in, pace/sense electrodes can also be placed epicardially on the right and left ventricles because the myocardial walls are thick enough to not be perforated in the process as also shown in the above-referenced Cazeau et al. article. In addition, a bi-ventricular pacemaker is proposed in the above-incorporated '259 patent having an array of ventricular pace/sense electrodes fitting about the apex of the heart to provide a plurality of usable epicardial pacing and/or sensing electrode sites about the apical region of the heart.

These approaches show promise in restoring the synchronous contractions of the right and left heart chambers in diseased hearts having significant conduction disturbances of the right and left heart depolarization waves but fail to preserve right and left heart synchrony in a physiologic manner. Significant conduction disturbances between the right and left atria can result in left atrial flutter or fibrillation that can be suppressed by pacing the left atrium synchronously with right atrial pacing of sensing of P-waves. And, left atrial and left ventricular cardiac output can be significantly improved when left and right chamber synchrony is restored, particularly in patients suffering from dilated cardiomyopathy.

SUMMARY OF THE INVENTION

The present invention is therefore directed to providing symmetrically operating right and left heart chamber pacing systems and methods of operation in two upper heart chambers or two lower heart chambers or three or four heart chambers that provide synchronous pacing of right and left heart chambers as needed. Such pacing systems of the present invention overcome the problems and limitations of the multiple chamber pacing systems described above and provide a great deal of flexibility in tailoring the delivered pacing therapy to needs of the individual patient's heart.

The present invention is also characterized herein as comprising multi-channel pacing systems having two, three or four pacing channels; each pacing channel includes a sense amplifier and pace output pulse generator coupled through a pacing lead with the pace/sense electrodes of each pacing channel located in relation to a heart chamber.

In accordance with the present invention, the synchronous pacing of one of the right and left heart chambers is provided on demand following expiration of programmable conduction delay windows (CDWs) that are started by both a paced event and a sensed event first occurring in the other of the right and left heart chambers. The delivery of the pacing pulse is inhibited by a sensed event detected in the other of the right and left heart chambers before the expiration of the CDW started by the paced event or sensed event first sensed in the other heart chamber. Advantageously, battery energy is not depleted by triggered pacing in the heart chamber where the spontaneous depolarization is first sensed.

The CDWs can be of the same length but preferably are programmable in length to take into account the type of event (paced event or sensed event) that commences them and the locations of the pace/sense electrodes with relation to the right and left heart chambers and their separation from one another. The programmed CDWs advantageously provide the optimum physiologic timing to sense depolarizations that are conducted to the second heart chamber from the first heart chamber that spontaneously depolarizes or is paced and to deliver a pacing pulse if the depolarization is not conducted within the CDW. The programmable CDW times can be selected to approximate normal, physiologic conduction delays or to provide a sequence of evoked depolarizations through pacing of the right and left heart chambers that compensates for a defect of the heart, e.g., a defective cardiac valve function.

More particularly, preferably a spontaneous, non-refractory, sensed event first sensed in one heart chamber before the expiration of an escape interval or an AV delay starts a sensed event CDW ($CDW^S$) for the sensing of a conducted depolarization in the other heart chamber. A pacing pulse delivered to one heart chamber at the expiration of an escape interval or an AV delay evokes a paced event and starts a paced event CDW ($CDW^P$) for the sensing of a conducted depolarization in the other heart chamber. Pacing in the other heart chamber is inhibited if a conducted depolarization is sensed as a sensed event within the $CDW^S$ or the $CDW^P$. Similarly, a pacing pulse is delivered to that heart chamber at the end of the $CDW^S$ or the $CDW^P$ if the $CDW^S$ or the $CDW^P$ times out without sensing a sensed event in that heart chamber. Each $CDW^S$ and $CDW^P$ for timing conduction of spontaneous or evoked depolarizations from the right and left heart chambers to the left and right heart chambers, respectively, is separately programmable in length. The provision of the separate sense $CDW^S$ and pace $CDW^P$ allows compensation for conduction delay differences that may exist in conduction of a depolarization that spontaneously occurs or is evoked by delivery of a pacing pulse. Such differences can arise due to physiology and/or arise from differences in the start of the evoked depolarization in response to the pace pulse applied to the first pair of pace/sense electrodes.

In the context of a two channel, bi-atrial or bi-ventricular, pacing system employing the present invention, an escape interval for timing delivery of pacing pulses in a bradycardia condition or the absence of any spontaneous depolarizations is provided. The escape interval is preferably timed from a previous paced event or sensed event in selected one heart chamber or a sensed event first occurring in either heart chamber. Thus, an asymmetry is introduced by the selection of the heart chamber to be first paced at the expiration of the escape interval. Advantageously, the selection of the heart chamber to be first paced and to commence the $CDW^P$ can be programmed to provide a pacing order that compensates for a cardiac defect. Or it can be programmed to provide the most physiologic pacing mimicking a normal electrical activation sequence between the pace/sense electrode location in relation to that selected heart chamber and the pace/sense electrode location in relation to the other heart chamber. Typically, the patient's heart would be assessed to determine which of the right or left heart chambers exhibits a normal electrical activation sequence, and that heart chamber would be selected to be first paced at the expiration of the pacing escape interval. For example, the heart chamber exhibiting a normal activation sequence would be selected to be first paced at the expiration of the escape interval in a heart that exhibits IACD, LBBB, or RBBB.

The present invention is also implemented in three or four channel pacing systems wherein AV synchrony is maintained between the upper and lower heart chambers and right and left heart chamber synchrony is maintained between one or both sets of the right and left heart chambers. AV synchrony is maintained between the three or four atrial and ventricular heart chambers by one or more programmable AV delay timed from an atrial paced or sensed event from the single or a selected one of the atrial pacing channels. A V-A escape interval is timed from a ventricular paced or sensed event from the single one or a selected one of the ventricular pacing channels. In each case, where right and left heart pacing channels are provided or programmed for use, a pacing pulse is delivered to one of the heart chambers at the expiration of the V-A escape interval or the AV delay. An atrial or a ventricular paced event $CDW^P$ is started for the sensing of a conducted depolarization in the other heart chamber. An atrial or a ventricular sensed event $CDW^S$ is started for the sensing of a conducted depolarization in the other heart chamber if a sensed event is detected within the V-A escape interval or the AV delay. Pacing in the other heart chamber is inhibited if a conducted depolarization is sensed as a sensed event within the $CDW^S$ or the $CDW^P$. Similarly, a pacing pulse is delivered to that heart chamber at the end of the $CDW^S$ or the $CDW^P$ if the $CDW^S$ or the $CDW^P$ times out without sensing a sensed event in that heart chamber. Each $CDW^S$ and $CDW^P$ for timing conduction of spontaneous or evoked depolarizations from the right and left heart chambers to the left and right heart chambers, respectively, is separately programmable in length.

In one three pacing channel embodiment, pace/sense electrodes are located in relation to either the right or left atrial heart chamber and both ventricular heart chambers, and pacing and sensing is provided to these heart chambers. In this embodiment, the AV delay is timed from an atrial paced event or sensed event, and the V-A escape interval can be programmed to be timed from either a right or left ventricular paced event or sensed event. In another three pacing channel embodiment, pace/sense electrodes are located in relation to both atrial heart chambers and to the right or left ventricular heart chambers, and pacing and sensing is provided to these heart chambers. In this embodiment, the AV delay is timed from a selected right or left atrial paced event or sensed event, and the V-A escape interval is timed from the ventricular paced event or sensed event.

In a full four pacing channel embodiment, right and left, atrial and ventricular sense amplifiers and pacing pulse output circuits are provided for sensing and pacing in all four heart chambers. The right or the left heart ventricular pacing channels are selected to control timing of the V-A pacing escape interval, and the right or left atrial pacing channels are selected to time out the AV delay, thereby introducing an asymmetry of operation. The full set of atrial and ventricular CDW timers are not employed or are selectively programmed ON and OFF to take into account either the normal right heart chamber-to-left heart chamber or left heart chamber-to-right heart chamber conduction delays correlated to the controlling right or left heart chamber.

The present invention also contemplates providing separately programmable AV delays which are started from both right and left atrial sensed and paced events, if both right and left atrial pacing channels are provided in the multi-channel pacing system. Moreover, both sensed and paced AV (SAV and PAV) delays are separately programmable and are started by right and/or left atrial paced events and sensed events and are terminated by a selected right or left ventricular sensed event. The commencement of the V-A escape interval can also be selected to be triggered by a right or left ventricular paced event or sensed event.

For example, in a patient suffering from abnormal right atrial-to-left atrial conduction delays, such as IACD or 2nd degree AV Block, the right atrium is selected as controlling the AV delay, and the right ventricle is selected as controlling the V-A escape interval. A left atrial $CDW^S$ that is programmed in length is started upon detection of a spontaneous intrinsic right atrial depolarization during the V-A escape interval, and a SAV delay is started. Similarly, a left atrial $CDW^P$ that is programmed in length is started upon delivery of a right atrial pace pulse at the end of the V-A escape interval, and a PAV delay is started. The delivery of the left atrial pace pulse is inhibited if a left atrial sensed event is detected during the time out of either the left atrial $CDW^S$ or the $CDW^P$, and a left atrial pace pulse is delivered if no atrial sensed event is detected before the left atrial $CDW^S$ or the $CDW^P$ times out. Subsequently, a ventricular pace pulse is delivered to the selected ventricular pace/sense electrodes if no ventricular sensed event is detected before the SAV or the PAV delay times out.

Similarly, in a patient suffering from abnormal right ventricle to left ventricle conduction delays, such as IVCD or 2nd degree AV Block, the right atrium is again selected as controlling the AV delay, and the right ventricle is selected as controlling the V-A escape interval. The appropriate SAV or PAV delay is started following either a right atrial sensed event occurring during the V-A escape interval or a right atrial paced event at the end of the V-A escape interval. A left ventricular sensed $CDW^S$ or paced $CDW^P$ is started upon detection of a spontaneous intrinsic right ventricular sensed event during the SAV or PAV delay or upon time out of the SAV or PAV delay. The delivery of the left ventricular pace pulse is inhibited if a left ventricular sensed event is detected during the time out of either the $CDW^S$ or the $CDW^P$, and a left ventricular pace pulse is delivered if no ventricular sensed event is detected before the $CDW^S$ or the $CDW^P$ times out.

These approaches advantageously avoid delivering pacing pulses substantially simultaneously to both the right and left heart chambers either in a triggered mode or in a synchronized mode as set forth in the prior art. A pacing pulse is delivered synchronously following the preceding sensed event or paced event at the termination of the $CDW^S$ or $CDW^P$ respectively. In certain patients suffering from congestive heart failure, the synchronously paced heart tends to recover its normal electrical activation sequence over time. Thus, this approach provides that if the recovery does occur, then the sensing of the normally conducted spontaneous or evoked depolarization inhibits the unnecessary delivery of pacing pulses.

In the dual chamber approaches, comprehensive right and left, atrial and ventricular synchronization is advantageously restored while the delivery of pacing pulses is minimized. In effect, physiologic conduction patterns are realized, competitive stimuli are eliminated, and battery longevity is enhanced due to non-redundant delivery of pacing pulses.

The present invention offers numerous advantages to patient's suffering from advanced congestive heart failure and exhibiting IACD, LBBB, RBBB, and/or IVCD. The introduction of the endocardial and/or epicardial right and left heart pacing leads and the implantation of the IPG are minimally invasive. Longevity is enhanced by the inhibition of the delivery of pacing pulses by sensed events detected within the respective controlling CDWs. The various operating modes of the IPG and the CDWs can be programmed during chronic implantation to adjust to observed changes in the underlying electrical activation sequence as the patient's condition improves or deteriorates.

The various embodiments of the present invention are preferably implemented into an implantable pulse generator and lead system selectively employing right and left heart, atrial and/or ventricular leads. However, they may also be implemented into an external pulse generator coupled with right and left heart, atrial and/or ventricular leads traversing the patient's skin. The various embodiments are implemented into an architecture that allows wide programming flexibility for operating in the above-described symmetric, right and left pacing channel configurations. Or asymmetric configurations can be configured in hard wired two, three and four channel circuitry or by selective programming of the active right and left pacing channels. The atrial channel that commences the SAV and PAV delays and the ventricular channel that terminates the SAV and PAV delays and controls the timing of the V-A escape interval can also be hard wired or programmed.

In order to realize the above configurations and the advantages flowing therefrom, the present invention preferably (but not necessarily) utilizes a low impedance field density clamp (FDC) sense amplifier which uses active detection circuitry to monitor the amount of current supplied to a selected pace/sense electrode. The supplied current changes the surface charge density to compensate for the electrode-electrolyte disturbance caused by the passage of a cardiac depolarization wavefront. This form of sensing is most sensitive to changes in charge distribution in a small volume of tissue located adjacent to the pace/sense electrode. This form of FDC sensing therefore is not strongly affected by far-field pace events, in contrast to high input impedance sense amplifiers. Thus, the delivery of a pace pulse to the pace/sense electrodes located in the left or right heart chamber will not mask a naturally conducted depolarization wave passing the pace/sense electrodes in the other heart chamber when it is sensed by the FDC sense amplifier coupled with those pace/sense electrodes.

In the context of a bi-atrial or bi-ventricular pacemaker, or both, the FDC sense amplifier is capable of detecting a naturally conducted depolarization wave within a wide range of programmed CDW times. Moreover, preferably (but not necessarily) the pacing output circuits are also configured as FDC circuits to generate the pacing pulses.

BRIEF DESCRIPTION OF THE DRAWINGS

These and other objects, advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

In the following detailed description, references are made to illustrative embodiments for carrying out the invention. It is understood that other embodiments may be utilized without departing from the scope of the invention. For example, the invention is disclosed in the context of two channel pacing system operating in demand and triggered pacing modes for restoring synchrony in depolarizations and contraction of left and right heart chambers for treating bradycardia in those chambers. The invention is also disclosed in the context of a four channel pacing system having an AV synchronous operating mode for restoring right and left heart chamber depolarization synchrony of the upper and lower heart chambers. The four channel pacing system is configurable to function as a three channel pacing system by selectively disabling one of the upper or lower pacing channels and associated logic circuitry for timing the $CDW^S$ and $CDW^P$. It should be appreciated that the present invention may be utilized to suppress atrial tachyarrhythmias noted in the above-incorporated Daubert articles and may in general be incorporated into an anti-tachyarrhythmia system including specific high rate pacing and cardioversion shock therapies for providing staged therapies to treat a diagnosed arrhythmia. It will also be appreciated that the two channel, three channel or four channel pacing systems and methods described herein in detail can be implanted and employed in treatment of an electrical conduction disturbance in a single heart chamber or between two heart chambers.

Figure 1:
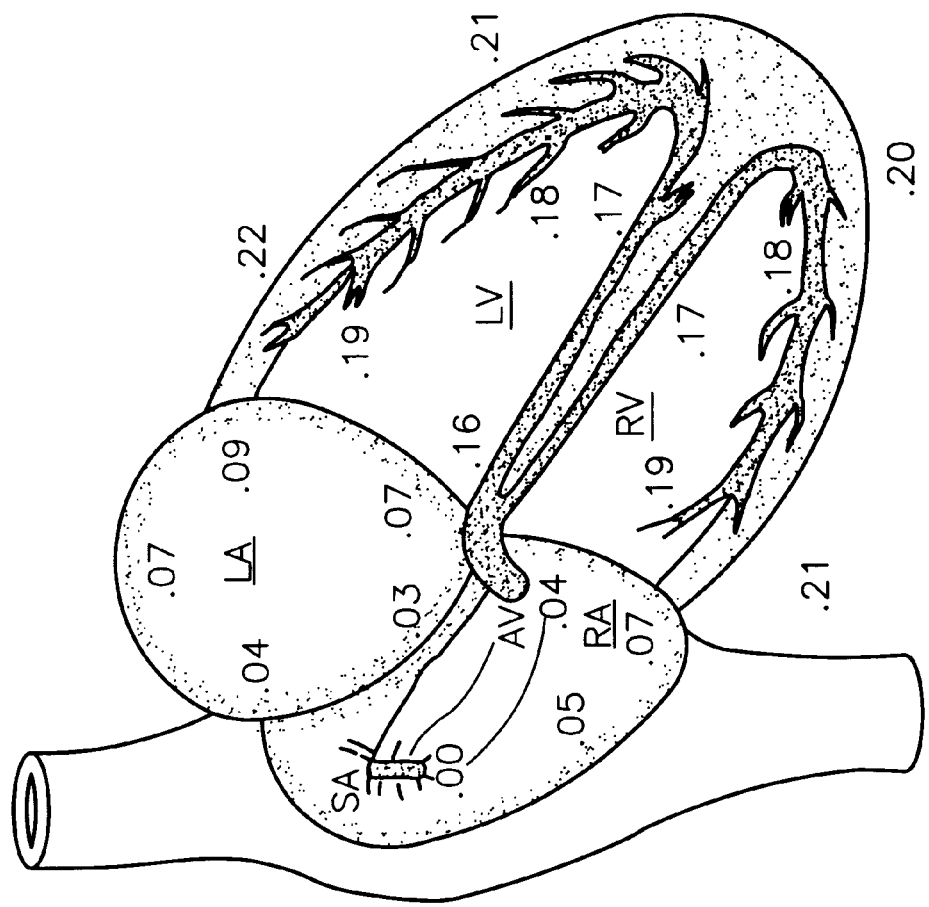
FIG. 1 is an illustration of transmission of the cardiac depolarization waves through the heart in a normal electrical activation sequence.

FIG. 1 is an illustration of transmission of the cardiac depolarization waves through the right atrium (RA), left atrium (LA), right ventricle (RV) and left ventricle (LV) of heart 10 in a normal electrical activation sequence at a normal heart rate with the conduction times exhibited thereon in seconds. The cardiac cycle commences normally with the generation of the depolarization impulse at the Sino-Atrial (SA) Node in the right atrial wall and its transmission through the atrial conduction pathways of Bachmann's Bundle and the Internodal Tracts at the atrial level into the left atrial septum. The RA depolarization wave reaches the Atrio-ventricular (AV) node and the atrial septum within about 40 msec and reaches the furthest walls of the RA and LA within about 70 msec, and the atria complete their contraction as a result. The aggregate RA and LA depolarization wave appears as the P-wave of the PQRST complex when sensed across external ECG electrodes and displayed. The component of the atrial depolarization wave passing between a pair of unipolar or bipolar pace/sense electrodes, respectively, located on or adjacent the RA or LA is also referred to as a sensed P-wave. Although the location and spacing of the external ECG electrodes or implanted unipolar atrial pace/sense electrodes has some influence, the normal P-wave width does not exceed 80 msec in width as measured by a high impedance sense amplifier coupled with such electrodes. A normal near field P-wave sensed between closely spaced bipolar pace/sense electrodes and located in or adjacent the RA or the LA has a width of no more than 60 msec as measured by a high impedance sense amplifier.

The depolarization impulse that reaches the AV Node is distributed inferiorly down the bundle of His in the intra-ventricular septum after a delay of about 120 msec. The depolarization wave reaches the apical region of the heart about 20 msec later and is then travels superiorly though the Purkinje Fiber network over the remaining 40 msec. The aggregate RV and LV depolarization wave and the subsequent T-wave accompanying re-polarization of the depolarized myocardium are referred to as the QRST portion of the PQRST cardiac cycle complex when sensed across external ECG electrodes and displayed. The highest amplitude component of the QRS ventricular depolarization wave passing between a pair of unipolar or bipolar pace/sense electrodes, respectively, located on or adjacent the RV or LV is referred to as the sensed R-wave. Although the location and spacing of the external ECG electrodes or implanted unipolar ventricular pace/sense electrodes has some influence, the normal R-wave width does not exceed 80 msec in width as measured by a high impedance sense amplifier. A normal near field R-wave sensed between closely spaced bipolar pace/sense electrodes and located in or adjacent the RV or the LV has a width of no more than 60 msec as measured by a high impedance sense amplifier.

The typical normal conduction ranges of sequential activation are also described in the article by Durrer et al., entitled "Total Excitation of the Isolated Human Heart", in CIRCULATION (Vol. XLI, pp. 899–912, June 1970). This normal electrical activation sequence becomes highly disrupted in patients suffering from advanced congestive heart failure and exhibiting IACD, LBBB, RBBB, and/or IVCD. These conduction defects exhibit great asynchrony between the RV and the LV due to conduction disorders along the Bundle of His, the Right and Left Bundle Branches or at the more distal Purkinje Terminals. Typical intra-ventricular peak—peak asynchrony can range from 80 to 160 msec or longer. In RBBB and LBBB patients, the QRS complex is widened far beyond the normal range to from >120 msec to 250 msec as measured on surface ECG. This increased width demonstrates the lack of synchrony of the right and left ventricular depolarizations and contractions.

In accordance with the present invention, a method and apparatus is provided to restore the depolarization sequence of FIG. 1 and the synchrony between the right and left, atrial and ventricular heart chambers that contributes to adequate cardiac output. This restoration is effected through providing optimally timed cardiac pacing pulses to each heart chamber as necessary and to account for the particular implantation sites of the pace/sense electrodes in relation to each heart chamber.

As noted in the above-referenced, commonly assigned, 09/067,751 application, now U.S. Pat. No. 5,902,324, it has been common in the prior art to use very high impedance P-wave and R-wave sense amplifiers to amplify the voltage difference signal which is generated across the pace/sense electrodes by the passage of a cardiac depolarization. The high impedance sense amplifiers use high gain to amplify the low amplitude signals and rely on pass band filters, time domain filtering and amplitude threshold comparison to discriminate a P-wave or R-wave from background electrical noise. Moreover, the sense amplifiers are uncoupled from the pace/sense electrodes during blanking periods of up to 100 msec after delivery of a pacing pulse to any of the pace/sense electrodes of the pacing system to avoid saturation of the sense amplifiers.

The present invention as described hereafter preferably uses low impedance FDC sense amplifiers, as described in the above-referenced, commonly assigned, 09/067,751 application, now U.S. Pat. No. 5,902,324, to be able to time out relatively short pace and sense CDWs. The FDC sense amplifier output pulses developed in response to a P-wave or R-wave passing by bipolar pace/sense electrodes are less than 10 msec in width, rather than the relatively long, 60–80 msec, P-waves and R-wave pulses sensed using the high impedance sense amplifiers. The FDC sense amplifiers provide very narrow output pulses as the P-wave or R-wave passes by the pace/sense electrodes coupled thereto and stabilize rapidly so that closely spaced, successive depolarization wavefronts passing by the pace/sense electrodes can be detected and distinguished from one another. Moreover, right and left heart chamber sense amplifier blanking intervals can be shortened to about the width of the pacing pulses which is typically 0.5–1.0 msec and up to about 10 msec. The blanking intervals can be minimized because of the ability of the right and left heart FDC sense amplifiers to discriminate between a pacing pulse artifact reflected across the pace/sense electrode pair and any closely following cardiac depolarization wavefront. Preferably, the blanking intervals are programmable so that they can be tailored after implantation and minimized to reflect the cardiac conduction conditions of the patient's heart.

Figure 2:
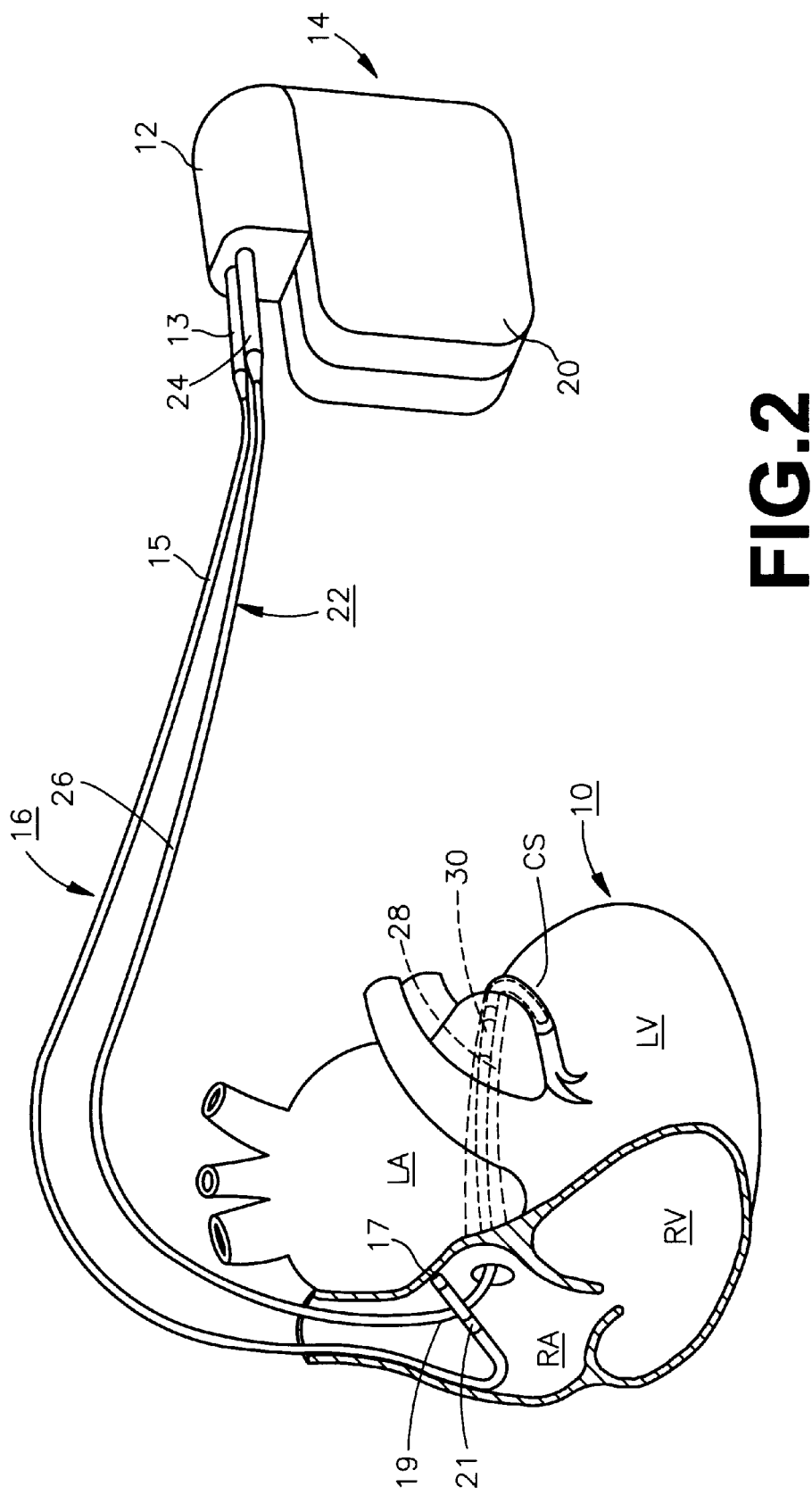
FIG. 2 is a schematic diagram depicting a two channel, bi-atrial pacing system in which the present invention is implemented.

FIG. 2 is a schematic representation of an implanted, two channel cardiac pacemaker of the above noted types for restoring synchronous contractions of the right and left atria. In FIG. 2, heart 10 includes the upper heart chambers, the right atrium (RA) and left atrium (LA), and the lower heart chambers, the right ventricle (RV) and left ventricle (LV) and the coronary sinus (CS) extending from the opening in the right atrium laterally around the atria to form the great vein that extends further inferiorly into branches of the great vein. The pacemaker IPG 14 is implanted subcutaneously, between the skin and the ribs. Bipolar, endocardial RA lead 16 and bipolar endocardial LA CS lead 22 are passed through a vein into the RA chamber of the heart 10 and into the CS to extend alongside the LA chamber. The RA lead 16 is formed with an in-line connector 13 fitting into a bipolar bore of IPG connector block 12 that is coupled to a pair of electrically insulated conductors within lead body 15 and connected with distal tip RA pace/sense electrode 19 and proximal ring RA pace/sense electrode 21. The distal end of the RA lead 16 is attached to the RA wall by an attachment mechanism 17. The LA CS lead 22 is formed with an in-line connector 24 fitting into a bipolar bore of IPG connector block 12 that is coupled to a pair of electrically insulated conductors within lead body 26 and connected with distal ring LA CS pace/sense electrode 30 and proximal ring LA CS pace/sense electrode 28. The distal end of the LA CS lead 26 is extended into the CS to position the LA CS pace/sense electrodes optimally with respect to the adjacent LA wall.

In operation, a P-wave sensed across either pair or one selected pair of the atrial pace/sense electrodes 17, 19 or 28, 30, is employed to reset the current A—A atrial escape interval and to start an atrial sense $CDW^S$ time. The A—A escape interval is typically timed from the right atrial paced and sensed events, but it can the left atrial paced and sensed events in appropriate circumstances. The right and left atrial sense $CDW^S$ lengths in msec are programmed to reflect the normal conduction delays of spontaneous atrial depolarizations between the atrial pace/sense electrodes 17, 19 and 28, 30 in a normal electrical activation sequence or to respond to a reverse activation sequence. An atrial pace pulse is delivered to the other pair of atrial pace/sense electrodes 17, 19 or 28, 30 to synchronize the right and left atrial depolarizations if the appropriate atrial $CDW^S$ time times out without the sensing of the P-wave at that other pair of the pace/sense electrodes. If the A—A atrial escape interval times out, then the atrial pace pulse is typically first delivered across the RA pace/sense electrodes 17, 19, and the paced atrial $CDW^P$ time is commenced. An atrial pace pulse is delivered to the LA CS pace/sense electrodes 28, 30 if the paced atrial $CDW^P$ times out without the sensing of the P-wave at the LA CS pace/sense electrodes 28 and 30.

Figure 3:
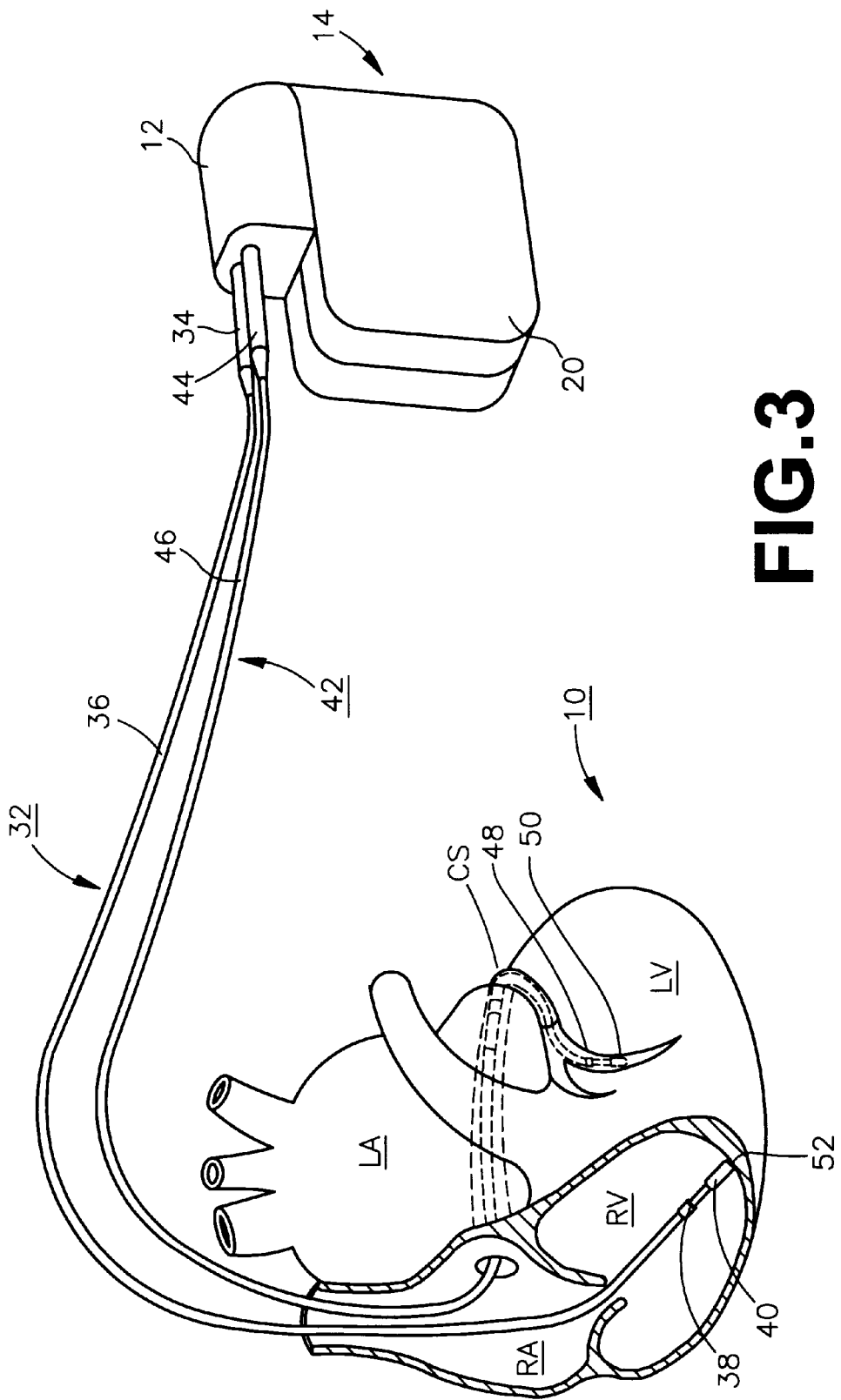
FIG. 3 is a schematic diagram depicting a two channel, bi-ventricular pacing system in which the present invention is implemented.

FIG. 3 is a schematic representation of an implanted, two channel cardiac pacemaker of the above noted types for restoring synchronous contractions of the right and left ventricles. Bipolar, endocardial LV CS lead 42 is passed through a vein into the RA chamber of the heart 10, into the CS and then inferiorly in the great vein and cardiac veins extending therefrom to extend the distal ring pace/sense electrodes 48 and 50 alongside the LV chamber. Bipolar, endocardial RV lead 32 is passed through the vein into the RA chamber of the heart 10 and into the RV where its distal ring and tip pace/sense electrodes 38 and 40 are fixed in place in the apex or in the interventricular septum by a distal attachment mechanism 52. The RV lead 32 is formed with an in-line connector 34 fitting into a bipolar bore of IPG connector block 12 that is coupled to a pair of electrically insulated conductors within lead body 36 and connected with distal tip pace/sense electrode 40 and proximal pace/sense ring electrode 38. The LV CS lead 42 is formed with an in-line connector 44 fitting into a bipolar bore of IPG connector block 12 that is coupled to a pair of electrically insulated conductors within lead body 46 and connected with distal ring pace/sense electrode 50 and proximal pace/sense ring electrode 48. The distal end of the LV CS lead 42 is extended into the CS to position the ring electrodes optimally with respect to the adjacent LV wall.

In operation, the R-wave sensed across one selected pair of the ventricular chamber pace/sense electrodes 38, 40 or 48, 50 is employed to reset the current V—V ventricular escape interval and to start a ventricular $CDW^S$. The V—V escape interval is typically timed from the right ventricular paced and sensed events, but it can be timed from the left ventricular paced and sensed events in appropriate circumstances. The right and left ventricular $CDW^S$ lengths in msec are programmed to reflect the normal conduction delays between the ventricular pace/sense electrodes 38, 40 and 48, 50 in a normal electrical activation sequence and in a reverse activation sequence. A ventricular pace pulse is delivered to the other pair of ventricular pace/sense electrodes to synchronize the right and left ventricular depolarizations if the right or left ventricular $CDW^S$ times out without the sensing of the R-wave at the other pair of the pace/sense electrodes 38, 40 or 48, 50. If the V—V ventricular escape interval does time out, then the ventricular pace pulse is typically first delivered across the RV pace/sense electrodes 38 and 40, and the ventricular pace $CDW^P$ is commenced. A ventricular pace pulse is delivered to the LV CS pace/sense electrodes 48 and 50 if the ventricular $CDW^P$ times out without the sensing of the R-wave at the LV CS pace/sense electrodes 48 and 50. As described further below, this order can be reversed in appropriate instances.

These illustrated RA and LA and RV and LV pace/sense leads and electrode locations are merely exemplary of possible leads and electrode locations that can be employed in the practice of these embodiments of the present invention. It will be understood that one or more of the other types of endocardial and epicardial leads and pace/sense electrodes located in or about the right and left chambers of the heart can be substituted for those illustrated in FIGS. 2 and 3 and described above.

Figure 4:
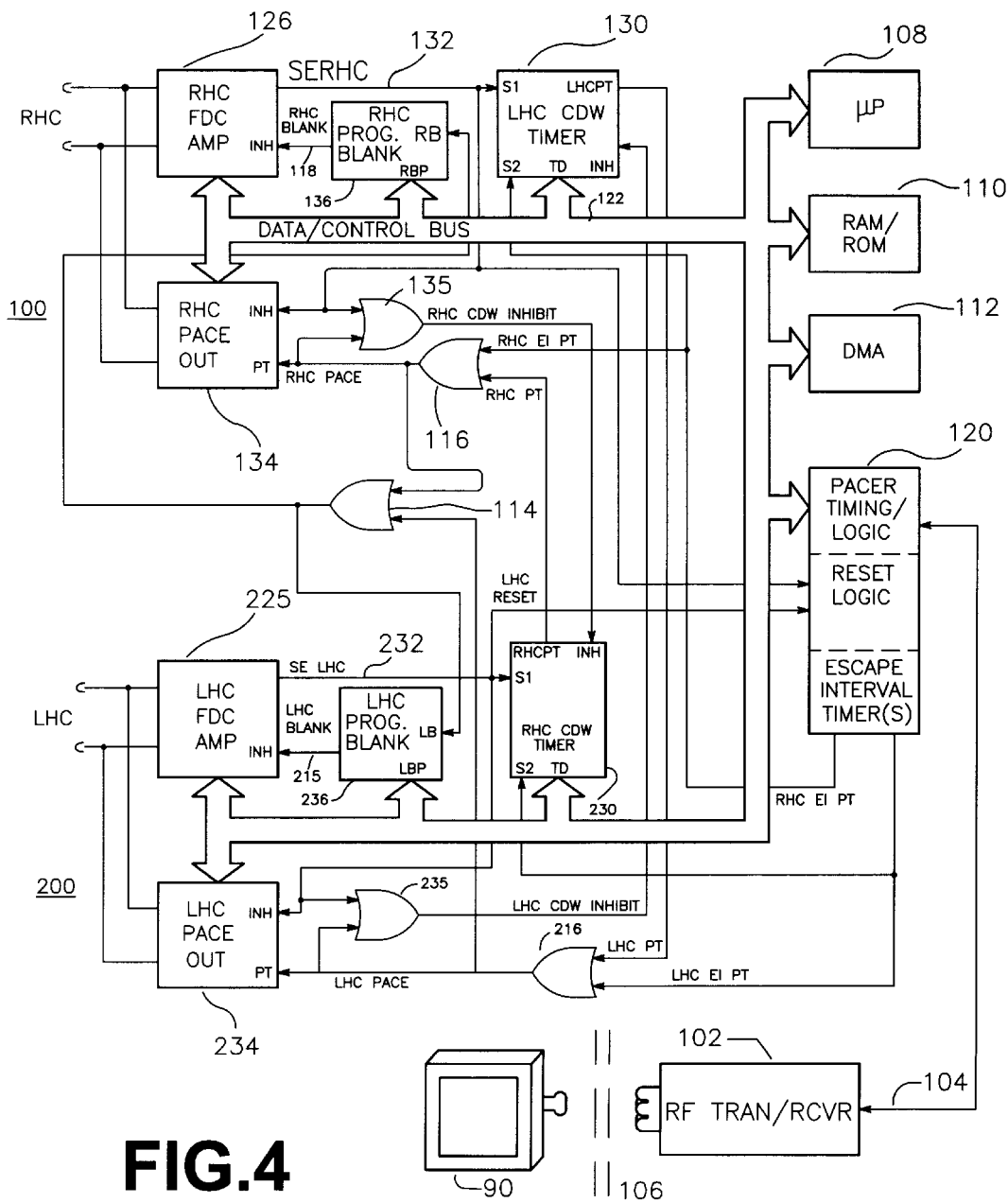
FIG. 4 is a simplified block diagram of the circuitry of the present invention for the two channel, right and left heart chamber, IPG employed in the systems of FIGS. 2 and 3.

In FIG. 4, the right heart chamber (RHC) and left heart chamber (LHC) designations are employed to embrace both bi-atrial and bi-ventricular contexts of use of a two channel pacing system of the present invention. Thus, FIG. 4 is a simplified block diagram of a two channel pacing system circuit comprising RHC circuitry 100 and LHC circuitry 200 and common components that can be employed to provide the pacing and sensing functions in a two channel, bi-atrial, pacemaker of FIG. 2 or bi-ventricular pacemaker of FIG. 3. Timing and control of the RHC and LHC circuitry 100 and 200 is realized through the software routines maintained in a microcomputer comprising the microprocessor 108, RAM/ROM chip 110, and DMA circuit 112 and in a pacer timing/logic circuit 120 coupled therewith. Operating modes and parameter values are programmed into RAM in RAM/ROM chip 110 through use of the external programmer 90 that transmits RF telemetry transmissions through the patient's skin to an antenna 106 and the RF telemetry transmitter/receiver 102 coupled with pacer timing/logic circuit 120. Such transcutaneous RF telemetry is well known in the art and allows programming of the operating modes, the A—A and V—V escape intervals and other timing and control intervals including the left and right channel $CDW^S$ and $CDW^P$ time lengths in accordance with the present invention.

Interconnections are provided between the RHC and LHC pacing and sensing circuitry 100 and 200 to perform the timing out of each $CDW^S$ and pacing if necessary to assure that the right and left heart chambers are depolarized and contract in the desired time relation to one another. The two channel IPG circuit of FIG. 4 is intended to comprehensively illustrate particular bi-atrial and bi-ventricular IPG circuits that may be employed to practice the various embodiments of the invention. The depicted RHC and LHC pacing and sensing circuitry 100 and 200 is fully symmetric. It will be understood that asymmetric two channel IPG circuits can be derived from the comprehensive two channel IPG circuit illustrated in FIG. 4 that function to treat unduly prolonged RHC-to-LHC conduction delays or LHC-to-RHC conduction delays. Such asymmetric two channel IPG circuits can be effected either by selectively disabling (through programming commands) or by simply physically eliminating unused components of the RHC or LHC circuitry 100 or 200. The components and logical interconnections illustrated in FIG. 4 are first described, and then the possible modifications are described.

With respect to the RHC circuitry 100, the RHC pace/sense terminals in the connector block 12 are coupled to the input terminals of RHC FDC amplifier 126 and to the output terminals of the RHC pacing pulse output circuit 134. Operating parameters of the RHC FDC amplifier 126 and the RHC pacing pulse output circuit 134 are set by programmed parameter values and operating modes provided on data/control bus 122. The RHC pacing pulse output circuit 134 delivers an RHC pacing pulse to the RHC terminals at a programmed pulse width and amplitude in response to an RHC PACE signal that is passed through OR gate 116. The RHC PACE signal is either the RHC pace trigger (RHC PT) signal generated by the RHC CDW timer 230 or the RHC escape interval pace trigger (RHC EI PT) signal generated by the escape interval timer in pacer timing/logic circuit 120.

An RHC BLANK signal is applied on line 118 to the RHC FDC amplifier 126 during and for a short period of less than 10 msec following delivery of an RHC or an LHC pacing pulse. The RHC BLANK signal is provided by RHC blanking circuit 136 in response to an RHC blanking trigger signal passed through OR gate 114 to the RB input. The OR gate 114 provides the RHC BLANK AND LHC BLANK trigger signals when a pacing pulse is triggered and delivered by either of the RHC and LHC pace output circuits 134 and 234. The OR gate 114 passes the RHC PACE and LHC PACE output signals of OR gate 116 and OR gate 216 which in turn pass the RHC pace trigger (RHC PT) and LHC pace trigger (LHC PT) signals that are generated by the time out of the escape interval or the programmable $CDW^S$ and $CDW^P$ times. The duration of the RHC BLANK signal is programmed into RAM/ROM chip 110 and retrieved and applied on data/control bus 122 to the RBP input of the programmable RHC blanking circuit 136. The RHC FDC amplifier 126 is thereby rendered incapable of responding to an RHC depolarization signal during the short time that an RHC BLANK signal is applied to it on line 118.

When the RHC BLANK signal is not present, the RHC FDC amplifier 126 responds to an RHC cardiac depolarization by providing a high amplitude, short duration sensed event RHC (SERHC) signal on line 132. The RHC FDC amplifier 126 responds to an RHC cardiac depolarization sensed across the RHC pace/sense electrodes. The RHC cardiac depolarization can originate spontaneously in the RHC or can originate spontaneously in the LHC or be evoked by an LHC pace pulse delivered to the LHC pace/sense electrodes and, in either case, be conducted to the RHC pace/sense electrodes in the RHC. The SERHC signal is provided to the programmable LHC CDW timer 130 to start timing out the programmed LHC $CDW^S$ time if the LHC CDW timer 130 is not inhibited at the time. The SERHC signal is also applied to the RHC inhibit input of the RHC pacing output circuit 134 to prevent it from operating and to the reset logic within pacer timing/logic circuit 120 to reset the escape interval timer. The escape interval timer is restarted by either the SERHC signal or the SELHC signal to generate either the RHC EI PT signal or the LHC escape interval pace trigger (LHC EI PT) signal on its expiration. The SERHC signal is also passed through the NOR gate 135 as the RHC CDW INHIBIT signal to reset and inhibit the RHC CDW timer as described below.

The LHC $CDW^S$ and $CDW^P$ time lengths are programmed into RAM/ROM chip 110 and retrieved and applied on data/control bus 122 to the TD input to the programmable LHC CDW timer 130. The programmable LHC CDW timer 130 starts timing out the programmed LHC $CDW^S$ time on receipt of the SERHC signal at start input S1. In addition, the programmable LHC CDW timer 130 starts timing out the programmed LHC $CDW^S$ time at the time that the RHC PACE signal is applied to the RHC pacing output circuit 134. This is effected by applying the RHC EI PT signal to a separate start input S2. It will be understood that the LHC CDW timer 130 may include redundant timers and selection logic to provide that a first LHC $CDW^S$ time may be started upon application of the SERHC signal at start input S1 and a second LHC $CDW^P$ time may be started upon application of the RHC EI PT signal to the start input S2. It will also be understood that the LHC CDW timer 130 may include programmable logic that responds to a programmed in selection command to disable response of the LHC CDW timer 130 to one or both of the SERHC and the RHC EI PT signals.

The programmable LHC CDW timer 130 generates an LHC PT signal if the LHC FDC amplifier 226 does not detect an LHC depolarization wave and generate the left heart chamber sensed event signal (SELHC) and LHC RESET command on line 232 before the programmed RHC $CDW^S$ or $CDW^P$ is timed out. The LHC PT signal is applied through OR gate 216 to the LHC PACE input of the LHC pacing pulse output circuit 234 which provides an LHC pacing pulse to the LHC terminals of the connector assembly 12. In this manner, the LHC pacing pulse is applied to the LHC terminals of the connector assembly 12 following the lapse of the LHC $CDW^P$ or $CDW^S$ following an RHC pacing pulse or a SERHC signal, respectively, to restore RHC-to-LHC synchrony.

The timing out of the programmable LHC $CDW^S$ or $CDW^P$ time by the LHC CDW timer 130 is halted and further triggering of the LHC timer 130 is inhibited by an LHC CDW INHIBIT signal applied to the inhibit (INH) input of LHC CDW timer 130. The LHC CDW INHIBIT signal is of a duration that is longer than any programmed CDW time but shorter than the pacing escape interval. The LHC CDW INHIBIT signal prevents the LHC CDW timer 130 from being restarted in response to a SERHC signal generated on sensing a depolarization that is conducted from the LHC pace/sense electrodes to the RHC pace/sense electrodes that is itself evoked by the LHC PT signal that it delivered to NOR gate 216. Consequently, the LHC PT signal is passed through the NOR gates 216 and 235 and applied to the INH input of LHC CDW timer 130. Similarly, the LHC CDW INHIBIT signal is generated by passage of the LHC EI PT signal or the SELHC signal through NOR gate 235 and applied to the INH input of the LHC CDW timer. Only the RHC CDW timer 230 should be started when these RHC paced and sensed events occur.

The LHC signal sensing and pacing output circuitry 200, in conjunction with NOR gates 114, 116 and 135, is configured and functions in a mirror image fashion to the RHC signal sensing and pacing output circuitry 100 described above. The LHC pace/sense terminals in the connector block 12 are coupled to the input terminals of LHC FDC amplifier 226 and to the output terminals of the LHC pacing pulse output circuit 234. A LHC BLANK signal is applied on line 218 to the LHC FDC amplifier 226 during the RHC PACE or LHC PACE signal as reflected through OR gate 114 and for a blanking time period thereafter. The LHC BLANK signal is provided by LHC blanking circuit 236 in response to an RHC blanking trigger signal generated by OR gate 114 and applied to the RB input. The duration of the LHC BLANK signal is programmed into RAM/ROM chip 110 and retrieved and applied on data/control bus 122 to the LBP input of the programmable LHC blanking circuit 236.

As in the case of the LHC CDW timer 130, it will be understood that the RHC CDW timer 230 includes redundant timers and selection logic to time the sense RHC $CDW^S$ started upon application of the SELHC signal at start input S1 and a pace RHC $CDW^P$ started upon application of the LHC EI PT signal to the start input S2. The programmable RHC CDW timer 230 starts timing out the programmed RHC $CDW^P$ time at the time that the LHC PACE signal is applied to the LHC pacing output circuit 234 if it is not inhibited. It will also be understood that the RHC CDW timer 230 may include programmable logic that responds to a programmed in selection command to disable response of the RHC CDW timer 230 to one or both of the SELHC and the LHC EI PT signals.

The LHC FDC amplifier 226 responds to an LHC cardiac depolarization sensed across the LHC pace/sense electrodes when it is not blanked by an LHC BLANK signal by providing a high amplitude, short duration sensed event signal SELHC on line 232. The LHC cardiac depolarization can originate spontaneously in the LHC or can originate spontaneously in the RHC or be evoked by an RHC pace pulse delivered to the RHC pace/sense electrodes and, in either case, be conducted to the LHC pace/sense electrodes in the LHC. The SELHC signal is provided to the S1 input of programmable RHC $CDW^S$ timer 230 to start timing out the programmed RHC $CDW^S$ time if it is not inhibited at the time. The SELHC signal is also applied to the LHC INH input of the LHC pacing output circuit 234 to prevent it from operating and to the reset logic within pacer timing/logic circuit 120 to reset the escape interval timer if the escape interval timer is programmed to respond to it. The SELHC signal is also applied as the INH input of the LHC CDW timer 130 through NOR gate 235, although it is not actually timing out an LHC CDW time in this scenario.

The programmable RHC CDW timer 230 generates an RHC PT signal at the time out of the RHC $CDW^S$ time if the RHC FDC amplifier 126 does not earlier detect an RHC depolarization wave and generate the SERHC signal. The RHC PT signal is applied through OR gate 116 to the RHC PACE input of the RHC pacing pulse output circuit 134 which provides a pacing pulse to the RHC pace/sense terminals of the connector assembly 12. However, if the SERHC signal is generated during the RHC $CDW^S$ time, it resets the RHC CDW timer 230 to terminate the RHC CDW time and inhibits the operation of the RHC CDW timer 230 from being restarted for a preset inhibition period in the manner described above.

The sensing characteristics of the RHC and LHC FDC amplifiers 126 and 226, the $CDW^S$ and $CDW^P$ times of the LHC and RHC CDW timers 130 and 230 and the RHC and LHC pacing pulse output circuits 134 and 234 can be separately programmed. The external programmer 90 is employed to provide the programmed modes and values via downlink telemetry with antenna 106 and RF transmitter/receiver 102 that are decoded and stored in RAM/ROM chip 110 in a manner well known in the art. Thus, while there is symmetry in the right and left heart chamber pacing and sensing circuitry, the operation can be made symmetric or asymmetric to optimize function in a given patient.

In the illustrated comprehensive two channel IPG circuit of FIG. 4, a single escape interval timer can be programmed with an escape interval value and programmed to generate the RHC EI PT signal or the LHC EI PT at the time out of the escape interval unless the escape interval is earlier restarted by a sensed RHC or LHC depolarization.

The normally functioning heart involves the depolarization and contraction of the right atrium first, the left atrium second and the right and left ventricles after the AV delay time as shown above with respect to FIG. 1. The interatrial conduction disturbances involve either a prolonged delay that may approach or exceed the AV delay or a complete dissociation of the right and left atrial contractions at all or certain heart rates. The interventricular conduction disturbances typically involve a retardation of the depolarization wave through the left ventricle outer wall which may be caused by damage to the conduction system and/or an enlarged heart muscle found in congestive heart chamber. Whatever the cause, in the typical case to be treated, the right heart chamber(s) contracts first, followed by the contraction of the left heart chamber(s) after the prolonged conduction delay. The converse situation does not arise typically but can occur as a result of premature atrial contractions arising in the left atrium. Thus, in this case, the IPG circuit of FIG. 4 can be programmed to operate in an asymmetric manner wherein the use of the LHC CDW timer 230 and is programmed OFF by a programmed in command or is eliminated entirely.

For example, the two channel IPG circuit components are capable of being programmed to respond to and treat unduly prolonged RHC-to-LHC conduction delays in the normal electrical activation sequence of FIG. 1 that occur due to IACD, LBBB, IVCD, RV Ectopic foci conduction patterns, RV pacing conduction patterns. In these cases, programmed in mode commands disable the RHC CDW timer 230, and the reset logic is programmed to only employ the SERHC signal to reset the escape interval timer. In addition, the escape interval timer only generates the RHC EI PT signal.

However, it will be realized that the two channel IPG circuit components are capable of being programmed to respond to and treat unduly prolonged LHC-to-RHC conduction delays in a reverse electrical activation sequence than the normal electrical activation sequence of FIG. 1 that occur due to RBBB, IVCD, LV Ectopic foci conduction patterns, and LV pacing conduction patterns. In these cases, programmed in mode commands disable the LHC CDW timer 130, and the reset logic is programmed to only employ the SELHC signal to reset the escape interval timer. In addition, the escape interval timer only generates the LHC EI PT signal. Of course, these configurations can be realized through a physical reduction of the components and interconnections of the comprehensive two channel circuit of FIG. 4.

Figure 5:
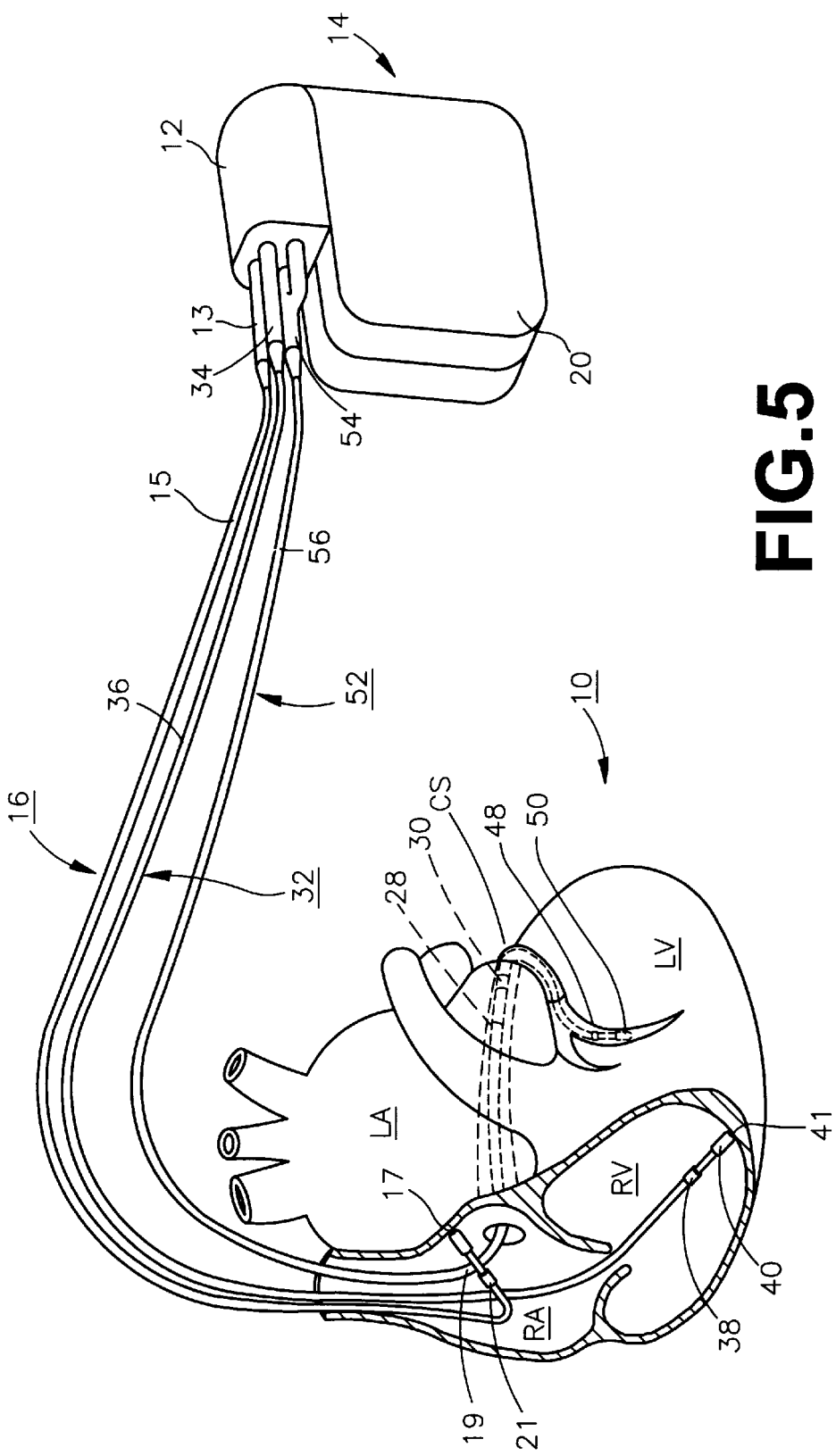
FIG. 5 is a schematic diagram depicting a three or four channel, bi-atrial and/or bi-ventricular, pacing system in which the present invention is implemented.

FIG. 5 is a schematic representation of an implanted, four channel cardiac pacemaker of the above noted types for restoring synchronous contractions of the right and left atria and the right and left ventricles. The in-line connector 13 of RA lead 16 is fitted into a bipolar bore of IPG connector block 12 and is coupled to a pair of electrically insulated conductors within lead body 15 that are connected with distal tip RA pace/sense electrode 19 and proximal ring RA pace/sense electrode 21. The distal end of the RA lead 16 is attached to the RA wall by a conventional attachment mechanism 17. Bipolar, endocardial RV lead 32 is passed through the vein into the RA chamber of the heart 10 and into the RV where its distal ring and tip RV pace/sense electrodes 38 and 40 are fixed in place in the apex by a conventional distal attachment mechanism 41. The RV lead 32 is formed with an in-line connector 34 fitting into a bipolar bore of IPG connector block 12 that is coupled to a pair of electrically insulated conductors within lead body 36 and connected with distal tip RV pace/sense electrode 40 and proximal ring RV pace/sense electrode 38.

In this case, a quadripolar, endocardial LV CS lead 52 is passed through a vein into the RA chamber of the heart 10, into the CS and then inferiorly in the great vein to extend the distal pair of LV CS pace/sense electrodes 48 and 50 alongside the LV chamber and leave the proximal pair of LA CS pace/sense electrodes 28 and 30 adjacent the LA. The LV CS lead 52 is formed with a four conductor lead body 56 coupled at the proximal end to a bifurcated in-line connector 54 fitting into a pair of bipolar bores of IPG connector block 12. The four electrically insulated lead conductors in LV CS lead body 56 are separately connected with one of the distal pair of LV CS pace/sense electrodes 48 and 50 and the proximal pair of LA CS pace/sense electrodes 28 and 30.

In operation, a P-wave sensed across the RA pace/sense electrodes 17 and 19 or the LA pace/sense electrodes 28 and 30 during the V-A escape interval timed from a preceding ventricular pacing pulse or R-wave sensed event is employed to start an AV delay and to start an LA $CDW^S$ or an RA $CDW^S$, respectively. An atrial pace pulse is delivered to the other pair of atrial pace/sense electrodes 17 and 19 or 28 and 30 if the respective LA or RA $CDW^S$ times out without the sensing of the same conducted P-wave at that other pair of the atrial pace/sense electrodes.

If the V-A atrial escape interval does time out without sensing a P-wave at either pair of atrial pace/sense electrodes 17 and 19 or 28 and 30, then the atrial pace pulse is typically first delivered across the RA pace/sense electrodes 17 and 19, and the respective LA $CDW^P$ time is commenced. Then, an atrial pace pulse is delivered to the LA CS pace/sense electrodes 28 and 30 only if the LA $CDW^P$ times out without the sensing of the P-wave at those pace/sense electrodes. However, it is also possible to program the reverse order of delivery so that the first atrial pace pulse is delivered to the LA CS pace/sense electrodes 28 and 30 at the expiration of the V-A atrial escape interval. Then, an atrial pace pulse is delivered to the RA pace/sense electrodes 17 and 19 only if the RA $CDW^P$ time times out without the sensing of the P-wave at the RA pace/sense electrodes.

It is proposed herein to employ separate programmable sense AV (SAV) delays that are employed depending on whether the first atrial sensed event is sensed across the RA pace/sense electrodes 17 and 19 or the LA CS pace/sense electrodes 28 and 30. Moreover, it is proposed to employ separate programmable paced AV (PAV) delays that are employed depending on whether the first atrial pacing pulsed is delivered across the RA pace/sense electrodes 17 and 19 or the LA CS pace/sense electrodes 28 and 30. These separately programmable RSAV and LSAV delays and RPAV and LPAV delays are provided to take into account the particular locations of the RA and LA pace/sense electrodes and the measured conduction time delays between those locations and the locations of the RV and LV pace/sense electrodes. This approach employing separate programmable RSAV and LSAV delays and separate programmable RPAV and LPAV delays is disclosed herein in reference to FIGS. 6 and 7 as one approach in which the present invention can be practiced. However, it will be understood that the present invention can be practiced employing a less complex approach using only a single, programmable AV delay or just one SAV delay and PAV delay.

Thus, in the preferred more complex case, an LSAV or RSAV or an LPAV or RPAV time is started on either sensing the first P-wave or on delivery of the first atrial pacing pulse to either the left or right atrial heart chamber. An R wave sensed across either of the RV or LV CS pace/sense electrodes 38 and 40 or 48 and 50 during the AV time delay is employed to reset the AV timer, to start a V-A escape interval, and to start a respective LV $CDW^S$ or RV $CDW^S$. A ventricular pace pulse is delivered to the other pair of RV or LV CS pace/sense electrodes 38 and 40 or 48 and 50 if the LV $CDW^S$ or RV $CDW^S$ times out without the sensing of the R-wave at the other pair of the RV or LV CS pace/sense electrodes.

Assuming that the normal activation sequence is sought to be restored, a single AV delay corresponding to a normal AV conduction time from the AV node to the bundle of His is programmed for use. If the AV delay time out, then the ventricular pace pulse is typically programmed to be first delivered across the RV pace/sense electrodes 38 and 40, and an LV $CDW^P$ is commenced. A left ventricular pace pulse is programmed to be delivered to the LV CS pace/sense electrodes 48 and 50 if the LV $CDW^P$ times out without the sensing of the R-wave at the LV-CS pace/sense electrodes 48 and 50.

Then, the sequence is repeated such that if the V-A escape interval time out, then an RA pace pulse is typically first delivered across the RA pace/sense electrodes 17 and 19, the AV delay timer is restarted, and the LA $CDW^P$ time is commenced. An LA pace pulse is delivered to the LA CS pace/sense electrodes 28 and 30 if the LA $CDW^P$ time times out without the sensing of the P-wave at the LA CS pace/sense electrodes 28 and 30.

Each AV delay and CDW can be programmed to restore the normal activation sequence taking the particular conduction disturbance and the location of the RA, LA, RV and LV pace/sense electrode locations into account. The activation sequence can also be modified to time these AV delays and CDWs from initial LA depolarizations arising from LA ectopic foci.

Figure 6:
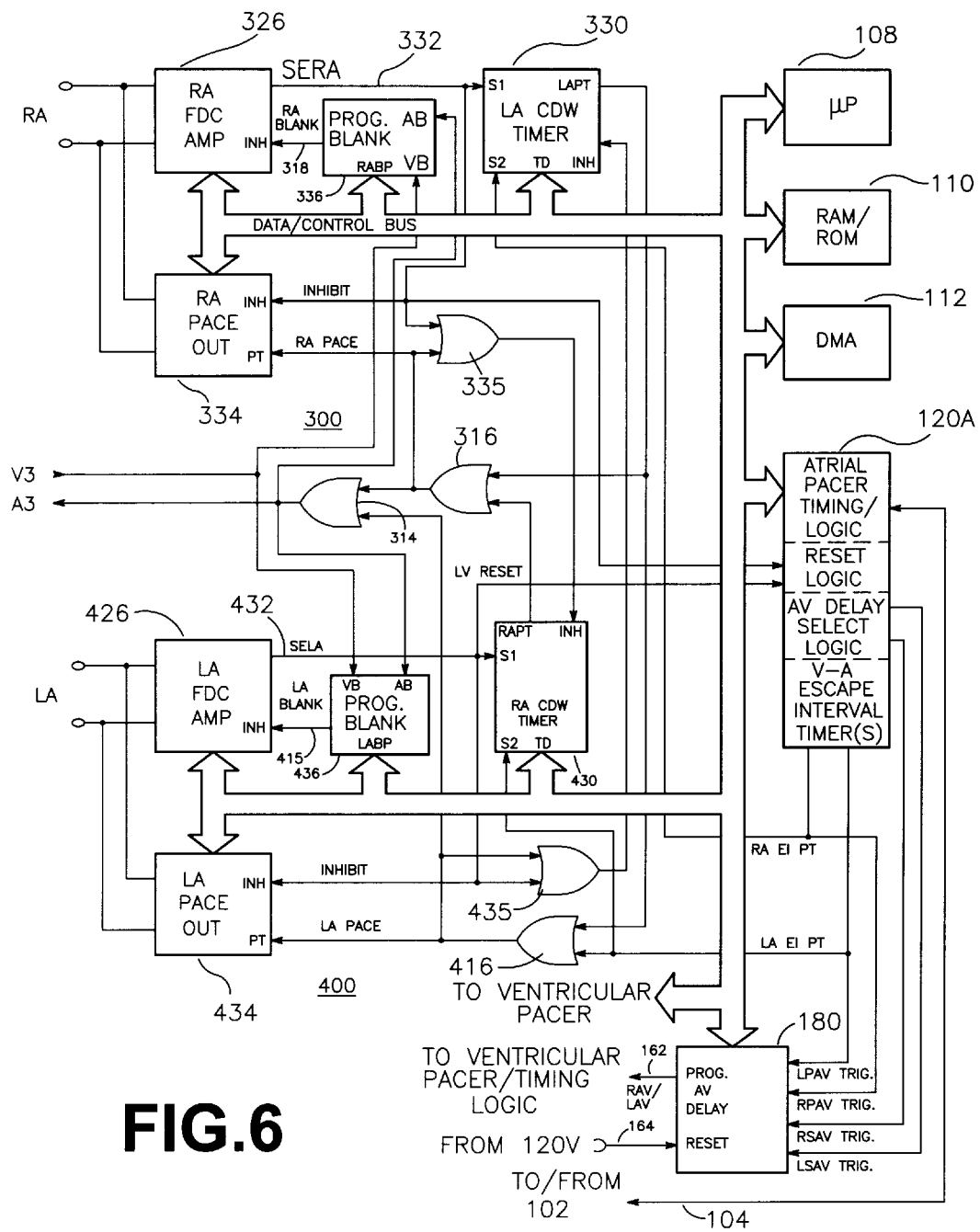
FIGS. 6 and 7 collectively are a simplified block diagrams of one embodiment of IPG circuitry of the present invention employed in the system of FIG. 5 for providing four pacing channels or selectively programming three pacing channels for selectively pacing right and left, upper and lower, heart chambers.
Figure 7:
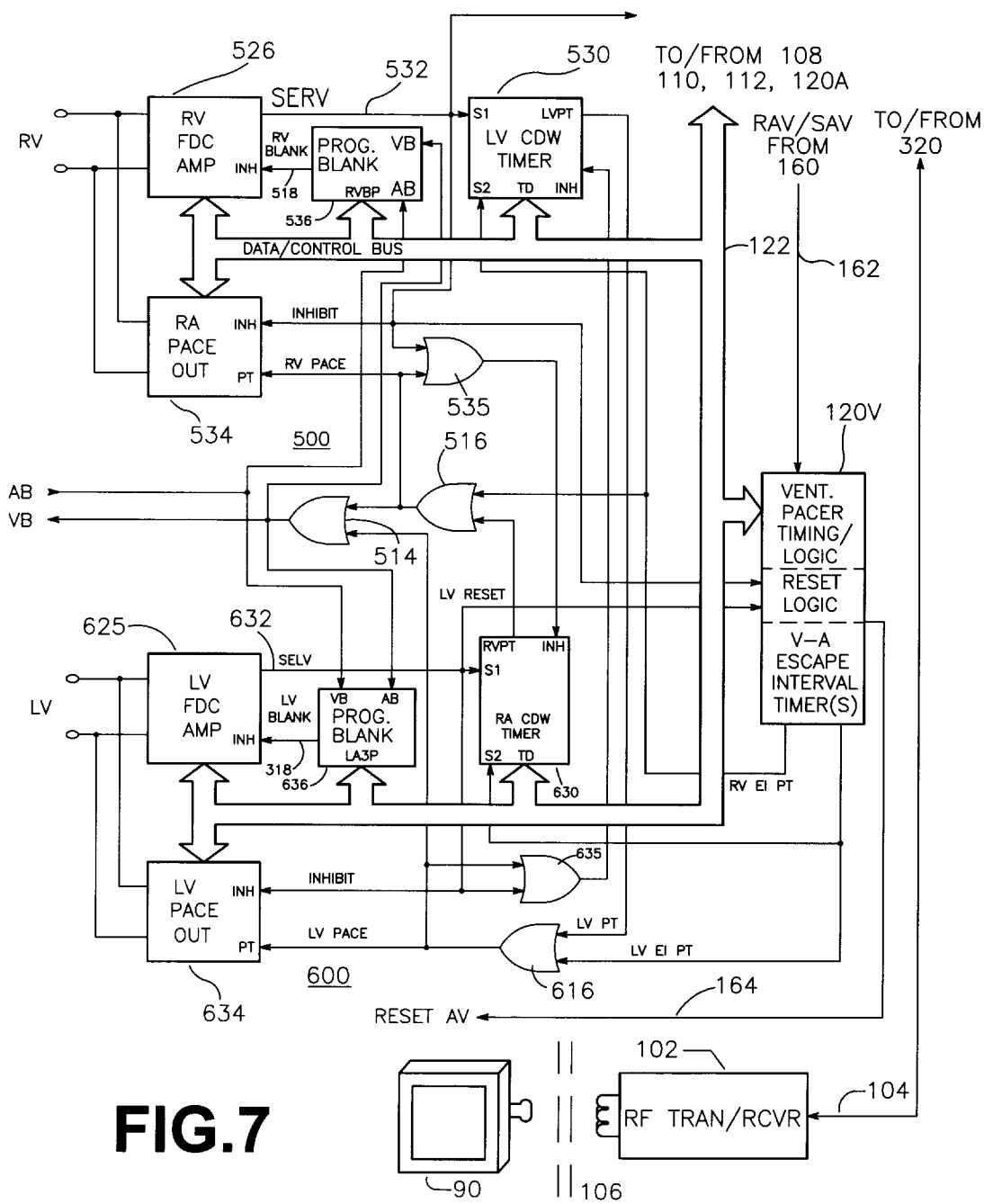

FIGS. 6 and 7 collectively are a simplified block diagram of a comprehensive, four channel IPG circuit of the present invention for the right and left heart chamber, four channel pacemaker IPG 14 employed in the system of FIG. 5. FIG. 6 illustrates the RA and LA pacing and sensing circuitry 300 and 400, respectively in relation to the data/control bus 122, the atrial pacer/timing logic circuit 120A, the microcomputer components 108,110,112 and the programmable AV delay logic 160. FIG. 7 illustrates the RV and LV pacing and sensing circuitry 500 and 600, respectively in relation to the data/control bus 122, the ventricular pacer/timing logic circuit 120V, the RF telemetry transmitter/receiver 102 and the external programmer 90. The microcomputer components 108,110,112 and the atrial pacer/timing logic circuit 120A of FIG. 6 are interconnected with the RV and LV pacing and sensing circuitry 500 and 600 and the ventricular pacer/timing logic circuit 120V of FIG. 7 via the data/control bus 122. The RF telemetry transmitter/receiver 102 of FIG. 7 is connected with the atrial pacer timing/logic circuit 120A of FIG. 6 via conductor 104, and the ventricular pace trigger output signal from programmable AV delay circuit 160 of FIG. 6 is coupled to the ventricular pacer/timing logic circuit 120V of FIG. 7 via the conductor 162. The atrial and ventricular pacer/timing logic circuit 120A and 120V and the programmable AV delay circuit 160 may alternatively be combined in a common circuit, as is conventional in DDD pacemakers.

The RA and LA pacing and sensing circuitry 300 and 400 and the RV and LV pacing and sensing circuitry 500 and 600 generally each follow the architecture of the RHC and LHC circuitry 100 and 200 of FIG. 4 described above in detail. The blanking circuitry differs somewhat in this four channel embodiment to allow for the blanking of all four of the RA, LA, RV and LV FDC sense amplifiers 326, 426, 526, 626 in response to delivery of a pace pulse by any of the RA, LA, RV and LV pace output circuits 334, 434, 534, 634. Each of the RA, LA, RV and LV programmable blanking circuits 336, 436, 536 and 636 generates a RA, LA, RV and LV BLANK signal on lines 318, 418, 518, and 618 having a duration programmed into RAM/ROM chip 110. The RA, LA, RV and LV BLANK signals are triggered by atrial blanking (AB) and ventricular blanking (VB) trigger signals generated at the outputs of OR gate 314 and OR gate 514, respectively.

The inputs of OR gate 314 are coupled with the outputs of OR gates 316 and 416 which provide the RA and LA PACE signals delivered to the RA and LA pace output circuits 334 and 434, respectively. The OR gates 316 and 416 pass the RA PT and LA PT signals selectively generated at the expiration of the V-A escape interval and the programmable CDWs timed by programmable time delays 330 and 430.

Similarly, the inputs of OR gate 514 are coupled with the outputs of OR gates 516 and 616 which provide the RV and LV PACE signals delivered to the RV and LV pace output circuits 534 and 634, respectively. The OR gates 516 and 616 pass the RV PT and LV PT signals selectively generated at the expiration of the AV delay and the programmable CDWs timed by LV and RV CDW timers 530 and 630.

In operation, assume that the V-A escape interval is being timed out from a preceding ventricular sensed or paced event, and that a spontaneous atrial depolarization occurs in one of the RA or LA and first passes by one of the RA pace/sense electrode pair 17, 19 or the LA CS pace/sense electrode pair 28, 30 (FIG. 5). The SERA signal or the SELA signal is generated when the P-wave is sensed across the pace/sense electrodes 17 and 19 or the LA CS pace/sense electrodes 28 and 30 by the RA FDC amplifier 326 or the LA FDC amplifier 426, respectively. The first of the SERA or SELA signal to occur during the timing out of the V-A escape interval is employed to reset the current V-A atrial escape interval being timed out in the atrial pacer timing/logic circuit 120A. The first occurring SERA or SELA signal also starts the timing of the respective RA or LA CDW$^S$ time by the respective RA or LA CDW timer 330 or 430. The first occurring SERA or SELA signal is also applied to reset the LA or RA CDW timer 430 or 330, respectively, which would not be timing out any CDW time under this circumstance. An atrial pace pulse is delivered to the other pair of atrial pace/sense electrodes by the RA or LA pacing output circuit 334 or 434 if the RA or LA CDW$^S$ times out without the sensing of the P-wave at the other of the RA or LA CS atrial pace/sense electrodes 17 and 19 or 28 and 30.

Assuming that the V-A escape interval does time out without a P-wave being sensed, then either an RA pace pulse or a LA pace pulse is delivered first by the respective RA pace output circuit 334 or LA pace output circuit 434, respectively, in response to the RA EI PT signal or the LA EI PT signal, respectively. The selection of which atrial pacing pulse is delivered can be programmed. If the RA pace pulse is delivered across the RA pace/sense electrodes 17 and 19, and the LA CDW time is commenced in LA CDW time timer 330. An atrial pace pulse is delivered to the LA CS pace/sense electrodes 28 and 30 if the RA CDW time times out without the sensing of the P-wave at the LA CS pace/sense electrodes 28 and 30.

In either case, the AV delay timer 160 is started to time out an AV time delay on sensing of the P-wave or delivery of the atrial pace pulse. As noted above, preferably separate programmable paced AV delays that are employed depending on whether the first atrial pacing pulsed is delivered across the RA pace/sense electrodes 17 and 19 or the LA CS pace/sense electrodes 28 and 30. These separately programmable RSAV and LSAV delays and RPAV and LPAV delays are provided to take into account the particular locations of the RA and LA pace/sense electrodes and the measured conduction time delays between those locations and the locations of the RV and LV pace/sense electrodes. In FIG. 6, these four possible delays are programmed "ON" or "OFF" and the delay values are programmed into RAM/ROM chip 110. The programmed delay values are used in the programmable AV delay timer 160 and started by one of the RSAV, LSAV trigger signals generated by the AV delay select logic or by one of the RPAV and LPAV trigger signals generated by the V-A escape interval timer(s) in atrial pacer timing/logic circuit 120A. Alternatively, only a single RAV or LAV delay can be triggered in response to the RSAV and RPAV trigger signals or the LSAV and LPAV trigger signals, respectively.

In the most general case, if an R-wave is sensed across one pair of the RV or LV CS pace/sense electrodes 38 and 40 or 48 and 50 during the AV time delay, the SERV or the SELV signal is generated by the RV FDC amplifier 526 or the LV FDC amplifier 626 and applied to reset logic in ventricular pacer timing/logic circuit 120V. A reset signal is generated on line 164 and employed to reset the AV delay timer 160 in FIG. 6. The SERV or the SELV signal is also employed to start a V-A escape interval in ventricular pacer timing/logic circuit 120V, and to start the ventricular CDW time in the respective RV or LV CDW timer 530 or 630. A ventricular pace pulse is delivered to the other pair of ventricular pace/sense electrodes by the respective RV or LV pacing output pulse generator 534 or 634 if the ventricular CDW time times out without the sensing of the R-wave at the other pair of the RV or LV CS pace/sense electrodes 38 and 40 or 48 and 50.

If the V-A escape interval times out, then the ventricular pace pulse is typically first delivered across the RV pace/sense electrodes 38 and 40, and the RV CDW time is commenced in RV CDW timer 530. A ventricular pace pulse is delivered to the LV CS pace/sense electrodes 48 and 50 by the LV pacing output circuit 634 if the ventricular CDW time times out without the sensing of the R-wave at the LV-CS pace/sense electrodes 48 and 50.

Again, in respect to the RA and LA atrial sensing and pacing circuits 300 and 400, the sensing characteristics of the RA and LA FDC amplifiers 326 and 426, the CDW times of the CDW time timers 330 and 430 and the pacing pulse output circuits 334 and 434 can be separately programmed and stored in RAM/ROM chip 110. Similarly, in respect to the RV and LV sensing and pacing circuits 500 and 600, the sensing characteristics of the RV and LV FDC amplifiers 526 and 626, the CDW times of the CDW timers 530 and 630 and the pacing pulse output circuits 534 and 634 can be separately programmed and stored in RAM/ROM chip 110. Moreover, either or both of the bi-ventricular and bi-atrial operating modes can be optionally programmed off to accommodate particular patients or changes in a particular patient's condition. For example, it may be possible to treat the above-referenced left atrial tachyarrhythmia by programming the above-described bi-atrial pacing mode on and selecting optimum atrial conduction time delays and programming the bi-ventricular pacing and sensing functions off. Conversely, the bi-atrial pacing and sensing functions may be selectively programmed off, and the bi-ventricular pacing and sensing functions optimally programmed to provide the proper therapy for a patient having normal interatrial conduction and abnormally long interventricular conduction delays.

Figure 8:
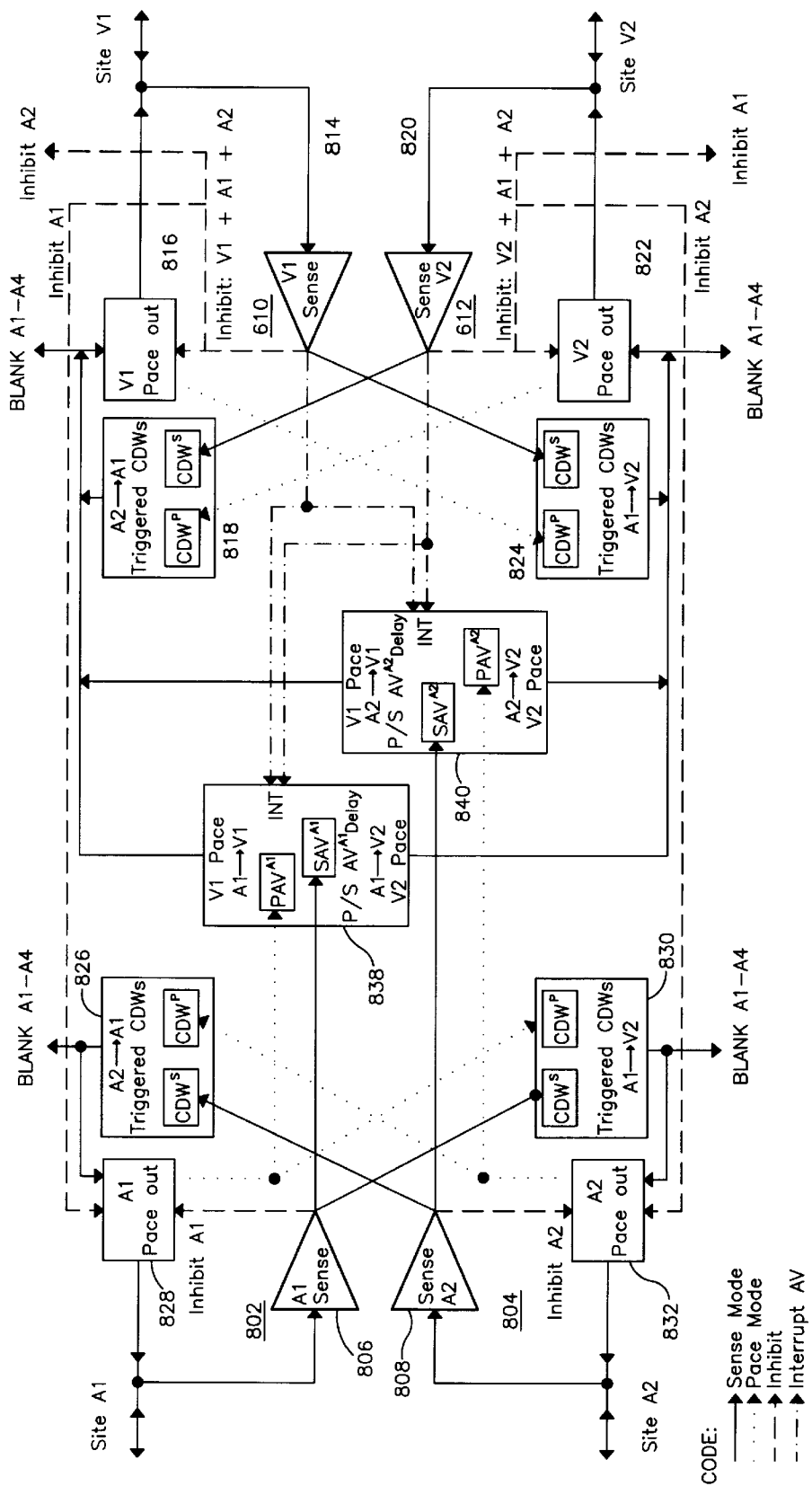
FIG. 8 is a simplified block diagram of a further embodiment of a multi-channel pacing system that can be configured to function as a two channel, three channel or four pacing channel pacing system.

FIG. 8 depicts a further simplified embodiment of a multi-channel pacing system 800 having A1 and A2 channels 802, 804 (which can be the RA and LA) and V1 and V2 channels 810, 812 (which can be the RV and LV). For convenience of illustration, blanking and refractory periods are not depicted and the escape interval timing block is not depicted. The depicted four channel pacing system 800 can be programmed to operate in a single channel (i.e., in a single heart chamber), a two channel, bi-atrial or bi-ventricular, pacing system or in a three channel system by disabling the un-used pacing channels and appropriate location of the pace/sense electrodes.

In a bi-atrial system comprising only atrial channels 802 and 804, it will be assumed that an A—A escape interval is continuously being reset and timed out. Atrial P-waves that are sensed by either the A1 atrial sense amplifier 806 or A2 atrial sense amplifier 808 reset the A—A escape interval and commence a Triggered $CDW^S$ in either the A1→A2 block 830 or the A2→A1 block 826, respectively. Similarly, the delivery of an A1 or A2 pace pulse at the end of the A—A escape interval by the A1 pace output 828 or the A2 pace output 832, respectively. resets the A—A escape interval and commences a Triggered $CDW^P$ in either the A1→A2 block 830 or the A2→A1 block 826, respectively. The A2 pace output 832 or the A1 pace output 828 is triggered at the end of the $CDW^S$ or the $CDW^P$ of block 830 or block 826, respectively, if the conducted atrial depolarization is not sensed by A2 sense amplifier 808 or A1 sense amplifier 806 before the $CDW^S$ or the $CDW^P$ times out.

In a bi-ventricular system only comprising ventricular channels 810 and 812, it will also be assumed that a V—V escape interval is continuously being reset and timed out. Ventricular R-waves that are sensed by either the V1 ventricular sense amplifier 814 or V2 ventricular sense amplifier 820 reset the V—V escape interval and commence a Triggered $CDW^S$ in either the V1→V2 block 824 or the V2→V1 block 818. Similarly, the delivery of V1 or V2 pace pulse at the end of the V—V escape interval by the V1 pace output 816 or V2 pace output 822, respectively, resets the V—V escape interval and commences a Triggered $CDW^P$ in either the V1→V2 block 824 or the V2→V1 block 818, respectively. The V2 pace output 822 or the V1 pace output 816 is triggered at the end of the $CDW^S$ or the $CDW^P$ if the conducted ventricular depolarization is not sensed by V2 sense amplifier 820 or V1 sense amplifier 814 before the $CDW^S$ or the $CDW^P$ times out.

When all channels of the four channel system 800 are enabled, a V-A escape interval is continuously being reset and timed out. It will be assumed that a V-A escape interval is timed from a selected V1 or V2 paced or sensed event that is reset by a selected A1 or A2 paced or sensed event. A spontaneous, non-refractory R-wave occurring during the time out of the V-A interval following a preceding ventricular sensed or paced event that is sensed by the V1 or V2 sense amplifiers starts a V1→V2 Triggered $CDW^S$ or a V2→V1 Triggered $CDW^S$ in blocks 824 and 818, respectively. Similarly, a spontaneous, non-refractory P-wave occurring during the time out of the V-A interval following a preceding ventricular sensed or paced event that is sensed by the A1 or A2 sense amplifiers starts an A1→A2 Triggered $CDW^S$ or an A2→A1 Triggered $CDW^S$ in blocks 830 and 826, respectively.

In a four channel configuration of multi-channel pacing system 800, the synchronized A→V pacing sequence following an A1 channel sensed or paced event can be selected to be A1→V1 or A1→V2. Similarly, the synchronized A→V pacing sequence following an A2 channel sensed or paced event can be selected to be A2→V1 or A2→V2. The $PAV^{A1}$ and $SAV^{A1}$ delays are started in AV Delay block 838 to be timed out by an A1 pace output or an A1 sensed event, respectively. If the $PAV^{A1}$ or $SAV^{A1}$ delay times out in block 838 without a V1 interrupt or V2 interrupt received from the V1 sense amplifier 814 or V2 sense amplifier 820, then either the V1 pace output 816 or the V2 pace output 822 is triggered, depending on the programmed sequence. Then, the $CDW^P$ in either the V2→V1 block 818 or V1→V2 block 824 is started to time out. The respective V1 pace output 816 or V2 pace output 822 is triggered to produce the V1 pace pulse or the V2 pace pulse unless a conducted R-wave is detected by the V1 sense amplifier 814 or the V2 sense amplifier 820 before the triggered $CDW^P$ times out. A similar operation takes place if the V1 interrupt or V2 interrupt is received from the V1 sense amplifier 814 or V2 sense amplifier 820 in response to a sensed R-wave. For example, the following sensed and paced mode sequences are illustrated in FIG. 8 assuming the A1→V1 pacing sequence is selected and a sensed event occurs in atrial channel 802:

SENSE MODE—Sensed event at A1 Sense Amplifier during V-A

A1 Sense Inhibits A1 Pace Output

A1 Sense Triggers A1→A2 $CDW^S$ in 830

A1→A2 $CDW^S$ times out at programmed msec

A1→A2 $CDW^S$ time out triggers A2 Pace Output 832

A1→A2 $CDW^S$ time out triggers BLANK

All Sense Amplifiers A1, A2, V1, V2 inhibited during BLANK

A2 Pace Output delivers triggered pace pulse to Site A2

A1 Sense Triggers $SAV^{A1}$ Delay in 838

$SAV^{A1}$ times out at programmed msec and triggers V1 Pace Output 816

V1 Pace Out triggers BLANK

All Sense Amplifiers A1, A2, V1, V2 inhibited during BLANK

V1 Pace Output 816 delivers triggered pace pulse to Site V1

$SAV^{A1}$ time out in 838 triggers V1→V2 $CDW^S$ in block 836

V1→V2 $CDW^S$ in block 836 times out at programmed msec

V1→V2 $CDW^S$ time out triggers V2 Pace Output 822

V1→V2 CDW$^S$ time out triggers BLANK
    All Sense Amplifiers A1, A2, V1, V2 inhibited during BLANK
    V2 Pace Output 822 delivers V2 pace pulse to Site V2
V1- V2 CDW$^S$ interrupted by V2 Sense
V1 Sense Interrupts SAV$^{A1}$ and Triggers V1→V2 CDW$^S$ in 836
    V1→V2 CDW$^S$ in block 836 times out at programmed msec
        V1→V2 CDW$^S$ time out triggers V2 Pace Output 822
        V1→V2 CDW$^S$ time out triggers BLANK
            All Sense Amplifiers A1, A2, V1, V2 inhibited during BLANK
            V2 Pace Output 822 delivers V2 pace pulse to Site V2 V1-V2 CDW$^S$ interrupted by V2 Sense
            PACE MODE—V-A escape interval times out
A1 Pace Output delivers A1 pace to Site A1
A1 Pace Triggers A1→A2 CDW$^P$ in 830
    A1→A2 CDW$^P$ times out at programmed msec
        A1→A2 CDW$^P$ time out triggers A2 Pace Output 832
        A1→A2 CDW$^P$ time out triggers BLANK
            All Sense Amplifiers A1, A2, V1, V2 inhibited during BLANK
            A2 Pace Output delivers triggered pace pulse to Site A2
A1 Pace Triggers PAV$^{A1}$ Delay in 838
    PAV$^{A1}$ times out at programmed msec and triggers V1 Pace Output 816
        V1 Pace Out triggers BLANK
            All Sense Amplifiers A1, A2, V1, V2 inhibited during BLANK
            V1 Pace Output 816 delivers triggered pace pulse to Site V1
PAV$^{A1}$ time out in 838 triggers V1→V2 CDW$^P$ in block 836
    V1→V2 CDW$^P$ in block 836 times out at programmed msec
        V1→V2 CDW$^P$ time out triggers V2 Pace Output 822
        V1→V2 CDW$^P$ time out triggers BLANK
            All Sense Amplifiers A1, A2, V1, V2 inhibited during BLANK
            V2 Pace Output 822 delivers V2 pace pulse to Site V2 V1-V2 CDW$^P$ interrupted by V2 Sense
V1 Sense Interrupts PAV$^{A1}$ and Triggers V1→V2 CDW$^S$ in 836
    V1→V2 CDW$^S$ in block 836 times out at programmed msec
        V1→V2 CDW$^S$ time out triggers V2 Pace Output 822
        V1→V2 CDW$^S$ time out triggers BLANK
            All Sense Amplifiers A1, A2, V1, V2 inhibited during BLANK
            V2 Pace Output 822 delivers V2 pace pulse to Site V2
V1-V2 CDW$^S$ interrupted by V2 Sense In similar manner, all of the conceivable A1 and A2 pace and sense modes for synchronous AV sequential pacing augmented with bi-atrial and bi-ventricular pacing can be practiced.

In any of these operating modes, the possibility exists that a pacing pulse will be delivered across the above-described right or left heart chamber pace/sense electrodes, and the delivered pacing pulse energy will appear across the other set of pace/sense electrodes masking the conducted P-wave or R-wave. This is particularly the case when relatively short CDW times are programmed to optimize timing of the synchronous depolarization of the right and left heart chambers and conventional high gain sense amplifiers are employed. Thus, each sense amplifier for each pacing channel will require its own specific programmable blanking periods to avoid this problem and the problem of saturation of the sense amplifiers. For conventional, high gain sense amplifiers, the blanking periods are programmed in the range of 100 msec. Much shorter blanking periods can be used with the FDC sense amplifiers. Refractory periods of the sense amplifiers are also programmable in the range of 20–350 msec for atrial channel sense amplifiers and 150–500 msec for ventricular channel sense amplifiers. During the refractory periods, sensed events will not be allowed to reset the pacing escape interval or AV delay being timed out.

The ability to sense a conducted evoked or spontaneous depolarization in one of the right or left heart chambers within a very short CDW from the pacing pulse or spontaneous depolarization to the other heart chamber is enhanced by use of FDC, right and left heart chamber, sense amplifiers. The FDC sense amplifier can be advantageously employed with conventional capacitive discharge pacing output circuits and short blanking periods. The blanking periods can be made even shorter using an FDC pacing output circuit which minimizes the pacing energy delivered and resulting after potentials on the delivery pace/sense electrodes. The use of the FDC circuit also minimizes the energy of the pacing artifact at the other pace/sense electrodes where the conducted evoked depolarization is to be sensed. In addition, the use of the FDC sense amplifier coupled with the pace/sense electrodes allows the morphology of spontaneous and evoked depolarizations conducted from a spontaneous or evoked depolarization in the other chamber to be analyzed to determine pathologies of the conduction pathways.

A preferred sense amplifier circuit for use in the above-described bi-chamber pacing systems as the FDC sense amplifier 126, 226, 326, 426, 526, 626 is described in detail in the above-referenced 09/067,751 application, now U.S. Pat. No. 5,902,324, and in commonly assigned U.S. Pat. Nos. 5,156,149, 5,233,985, and 5,370,665 by Hudrlik, which are incorporated by reference herein in their entireties. The active circuitry of the FDC sense amplifier circuit attempts to maintain an equilibrium condition between the pace/sense electrodes. The field perturbation caused by the passing cardiac depolarization or pacing artifact wavefront is nulled out by the active circuitry which attempts to maintain a fixed relationship between the potentials at the pace/sense electrodes coupled to the terminals. In doing so, a very fast rise time, narrow voltage signal is generated that can be used in peak detection or threshold comparison to precisely identify the time of occurrence of the depolarization.

In the above preferred embodiments, it will be understood that the use of the FDC sense amplifier allows the programming of each CDW$^S$ and CDW$^P$ in a range of from 0 msec to any preferred upper limit. A sensed or paced event in one of the right or left heart chambers triggers substantially simultaneous delivery of a pacing pulse to the other heart chamber when the CDW$^P$ and CDW$^S$ is programmed at 0 msec. The maximum programmable CDW$^S$ and CDW$^P$ is envisaged to be about 100 msec to account for the physiologic activation sequence conduction delays illustrated in FIG. 1. Or a long CDW can be programmed to allow sensing the conducted depolarization and measuring the actual pace triggered or spontaneous conduction delay between any pair of right and left heart chamber pace/sense electrodes. Or the long CDW can be programmed in cases where conduction between right and left heart chambers is absent to provide a highly delayed delivery of a pacing pulse following a sensed or paced event in one heart chamber to the other heart chamber to achieve a particular therapeutic timing of depolarizations of the right and left heart chambers.

Although bipolar atrial and/or ventricular lead systems are depicted in the drawing figures and described above, it will be understood that the present invention may be employed with unipolar lead systems that employ a single pace/sense electrode in the depicted positions in or about the right and left heart chambers and a remote electrode 20 formed as part of the outer surface of the housing of the IPG 12 in FIGS. 2, 3 and 5. Moreover other leads and pace/sense electrodes may be used instead of the depicted leads and pace/sense electrodes that are adapted to be placed at electrode sites on or in the RA, LA, RV and LV.

The preceding specific embodiments are illustrative of the practice of the invention. It is to be understood, therefore, that other expedients known to those of skill in the art or disclosed herein may be employed. In the following claims, means-plus-function clauses are intended to cover the structures described herein as performing the recited function and not only structural equivalents but also equivalent structures. For example, although a nail and a screw may not be structural equivalents in that a nail employs a cylindrical surface to secure wooden parts together, whereas a screw employs a helical surface, in the environment of fastening wooden parts, a nail and a screw are equivalent structures.

It is therefore to be understood, that within the scope of the appended claims, the invention may be practiced otherwise than as specifically described without actually departing from the spirit and scope of the present invention.

We claim:

1. A pacing system for improving the hemodynamic efficiency of a sick heart suffering from conduction delays in conducting spontaneous or evoked depolarizations originating in one of the right or left heart chamber to the other of the left or right heart chamber comprising:

right heart lead means for locating first and second right heart chamber pace/sense electrodes in relation with the right heart chamber;

left heart lead means for locating first and second left heart chamber pace/sense electrodes in relation with the left heart chamber;

right heart chamber depolarization sensing means coupled with said right heart chamber lead means for sensing spontaneous cardiac depolarizations originating in the right heart chamber and conducted cardiac depolarizations originating in the left heart chamber from a spontaneous cardiac depolarization or delivery of a left heart pacing pulse to the left heart chamber and for providing a right heart chamber sensed event signal in response to either a sensed spontaneous or conducted cardiac depolarization;

left heart chamber depolarization sensing means coupled with said left heart chamber lead means for sensing spontaneous cardiac depolarizations originating in the left heart chamber and conducted cardiac depolarizations originating in the right heart chamber from a spontaneous cardiac depolarization or delivery of a right heart pacing pulse to the right heart chamber a paced event and for providing a left heart chamber sensed event signal in response to either a sensed spontaneous or conducted cardiac depolarization;

escape interval timing means for timing an escape interval establishing a pacing rate and providing an escape interval pace trigger signal at the time out of the escape interval, the escape interval timing means further comprising reset means for restarting the timing of the escape interval in response to one of the right or left heart chamber sensed event signals;

right heart pacing pulse output means coupled with said right heart chamber lead means and selectively responsive to an applied pace trigger signal for generating and delivering a right heart pacing pulse to said right heart chamber lead means to evoke a right heart chamber depolarization;

left heart pacing pulse output means coupled with said left heart chamber lead means and selectively responsive to an applied pace trigger signal for generating and delivering a left heart pacing pulse to said left heart chamber lead means to evoke a left heart chamber depolarization;

means for applying said escape interval pace trigger signal to one of said right heart pacing pulse output means or said left heart pacing pulse output means;

left heart chamber conduction delay window timing means coupled with said escape interval timing means and said right heart chamber depolarization sensing means for timing a left heart chamber conduction delay window from a right heart chamber sensed event signal and selectively from an escape interval pace trigger signal and for providing a left heart chamber pace trigger signal at the expiration of the left heart chamber conduction delay window time, said left heart chamber conduction delay window timing means further coupled with said left heart chamber depolarization sensing means and comprising left heart chamber window terminating means for terminating the timing out of the left heart chamber conduction delay window in response to a left heart chamber sensed event signal;

means for applying said left heart chamber pace trigger signal to said left heart pacing pulse output means as a pace trigger signal for triggering the generation and delivery of a left heart pacing pulse to said left heart chamber lead means;

right heart chamber conduction delay window timing means coupled with said escape interval timing means and said left heart chamber depolarization sensing means for timing a right heart chamber conduction delay window from a left heart chamber sensed event signal and selectively from an escape interval pace trigger signal and for providing a right heart chamber pace trigger signal at the expiration of the right heart chamber conduction delay window time, said right heart chamber conduction delay window timing means further coupled with said right heart chamber depolarization sensing means and comprising right heart chamber window terminating means for terminating the timing out of the right heart chamber conduction delay window in response to a right heart chamber sensed event signal; and means for applying said right heart chamber pace trigger signal to said right heart pacing pulse output means as a pace trigger signal for triggering the generation and delivery of a right heart pacing pulse to said right heart chamber lead means;

whereby an excessive conduction delay between a spontaneous or evoked depolarization in the right heart chamber and the conducted depolarization wave in the left heart chamber or an excessive conduction delay between a spontaneous or evoked depolarization in the left heart chamber and the conducted depolarization wave in the right heart chamber is corrected by generation and delivery of a pacing pulse to the left or right heart chamber, respectively at the timing out of the corresponding conduction delay window.

2. The pacing system of claim 1, further comprising:

means for selecting one of the right or left heart chamber sensed event signals for use by said reset means to restart the escape interval.

3. The pacing system of claim 2, further comprising:

means for selectively disabling said right heart chamber conduction delay window timing means to configure said pacing system to only provide said left heart chamber pace trigger signal for treating an abnormal conduction delay from the right heart chamber to the left heart chamber; and means for selectively disabling said left heart chamber conduction delay window timing means to configure said pacing system to only provide said right heart chamber pace trigger signal for treating an abnormal conduction delay from the left heart chamber to the right heart chamber.

4. The pacing system of claim 3, further comprising:

right heart chamber blanking means coupled with said right heart chamber depolarization sensing means for preventing the sensing of spontaneous and evoked cardiac depolarizations in the right heart chamber and provision of a right heart chamber sensed event signal for the duration of a right heart chamber blanking period;

left heart chamber blanking means coupled with said left heart chamber depolarization sensing means for preventing the sensing of spontaneous and evoked cardiac depolarizations in the left heart chamber and provision of a left heart chamber sensed event signal for the duration of a left heart chamber blanking period; and means for triggering operation of said right and left heart chamber blanking means in response to the generation of a right heart pacing pulse and a left heart pacing pulse.

5. The pacing system of claim 1, further comprising:

means for applying one of the right or left heart chamber sensed event signals to said reset means to restart the escape interval timer; and means for applying said escape interval pace trigger signal to one of the right or left heart chamber pacing pulse output means to generate a right or left heart chamber pacing pulse upon the time out of the escape interval.

6. The pacing system of claim 5, further comprising:

right heart chamber blanking means coupled with said right heart chamber depolarization sensing means for preventing the sensing of spontaneous and evoked cardiac depolarizations in the right heart chamber and provision of a right heart chamber sensed event signal for the duration of a right heart chamber blanking period;

left heart chamber blanking means coupled with said left heart chamber depolarization sensing means for preventing the sensing of spontaneous and evoked cardiac depolarizations in the left heart chamber and provision of a left heart chamber sensed event signal for the duration of a left heart chamber blanking period; and means for triggering operation of said right and left heart chamber blanking means in response to the generation of a right heart pacing pulse and a left heart pacing pulse.

7. The pacing system of claim 1, further comprising:

right heart chamber blanking means coupled with said right heart chamber depolarization sensing means for preventing the sensing of spontaneous and evoked cardiac depolarizations in the right heart chamber and provision of a right heart chamber sensed event signal for the duration of a right heart chamber blanking period;

left heart chamber blanking means coupled with said left heart chamber depolarization sensing means for preventing the sensing of spontaneous and evoked cardiac depolarizations in the left heart chamber and provision of a left heart chamber sensed event signal for the duration of a left heart chamber blanking period; and means for triggering operation of said right and left heart chamber blanking means in response to the generation of a right heart pacing pulse and a left heart pacing pulse.

8. The pacing system of claim 1, further comprising:

means for programming said left heart chamber conduction delay window in a range of 0–100 msec; and means for programming said right heart chamber conduction delay window in a range of 0–100 msec.

9. A pacing method for improving the hemodynamic efficiency of a sick heart suffering from conduction delays in conducting spontaneous or evoked depolarizations originating in one of the right or left heart chamber to the other of the left or right heart chamber comprising the steps of:

locating first and second right heart chamber pace/sense electrode in relation with the right heart chamber;

locating first and second left heart chamber pace/sense electrodes in relation with the left heart chamber;

sensing spontaneous and evoked cardiac depolarizations in the right heart chamber across said right heart chamber pace/sense electrodes and providing a right heart chamber sensed event signal;

sensing spontaneous and evoked cardiac depolarizations in the left heart chamber across said left heart chamber pace/sense electrodes and providing a left heart chamber sensed event signal;

timing an escape interval establishing a pacing rate and providing an escape interval pace trigger signal at the time out of the escape interval;

restarting the timing of the escape interval in response to one of the right or left heart chamber sensed event signals;

in response to the escape interval pace trigger signal, selectively triggering either right heart pacing pulse output means coupled with said right heart chamber pace/sense electrodes to generate and deliver a right heart pacing pulse to said right heart chamber pace/sense electrodes to evoke a right heart chamber depolarization or left heart pacing pulse output means coupled with said left heart chamber pace/sense electrodes to generate and deliver a left heart pacing pulse to said left heart chamber lead means to evoke a left heart chamber depolarization;

timing a left heart chamber conduction delay window from a right heart chamber sensed event signal or from generation of a right heart pacing pulse and providing a left heart chamber pace trigger signal at the expiration of the left heart chamber conduction delay window;

terminating the timing out of the left heart chamber conduction delay window in response to a left heart chamber sensed event signal;

applying said left heart chamber pace trigger signal to said left heart pacing pulse output means to trigger the generation and delivery of a left heart pacing pulse to said left heart chamber lead means;

timing a right heart chamber conduction delay window from a left heart chamber sensed event signal or from generation of a left heart pacing pulse and providing a right heart chamber pace trigger signal at the expiration of the right heart chamber conduction delay window;

terminating the timing out of the right heart chamber conduction delay window in response to a right heart chamber sensed event signal; and applying said right heart chamber pace trigger signal to said right heart pacing pulse output means to trigger the generation and delivery of a right heart pacing pulse to said right heart chamber lead means;

whereby an excessive conduction delay between a spontaneous or evoked depolarization in one of the right or left heart chamber and the conducted depolarization wave in the other of the left or right heart chamber is corrected by generation and delivery of a pacing pulse at the timing out of the conduction delay window.

10. The pacing method of claim 9, further comprising the step of:

selecting one of the right or left heart chamber sensed event signals for use by said reset means.

11. The pacing method of claim 10, further comprising the steps of:

selectively disabling said right heart chamber conduction delay window timing means to configure said pacing system to only provide said left heart chamber pace trigger signal for treating an abnormal conduction delay from the right heart chamber to the left heart chamber; and selectively disabling said left heart chamber conduction delay window timing means to configure said pacing system to only provide said right heart chamber pace trigger signal for treating an abnormal conduction delay from the left heart chamber to the right heart chamber.

12. The pacing method of claim 11, further comprising the steps of:

preventing the sensing of spontaneous and evoked cardiac depolarizations in the right heart chamber and the provision of a right heart chamber sensed event signal in response thereto for the duration of a right heart chamber blanking period in response to the generation of a right heart pacing pulse and a left heart pacing pulse; and preventing the sensing of spontaneous and evoked cardiac depolarizations in the left heart chamber and the provision of a left heart chamber sensed event signal in response thereto for the duration of a left heart chamber blanking period in response to the generation of a right heart pacing pulse and a left heart pacing pulse.

13. The pacing method of claim 9, further comprising the steps of:

employing one of the right or left heart chamber sensed event signals to restart the timing of the escape interval; and applying said escape interval pace trigger signal to one of the right or left heart chamber pacing pulse output means to generate a right or left heart chamber pacing pulse upon the time out of the escape interval.

14. The pacing method of claim 13, further comprising the steps of:

preventing the sensing of spontaneous and evoked cardiac depolarizations in the right heart chamber and the provision of a right heart chamber sensed event signal in response thereto for the duration of a right heart chamber blanking period in response to the generation of a right heart pacing pulse and a left heart pacing pulse; and preventing the sensing of spontaneous and evoked cardiac depolarizations in the left heart chamber and the provision of a left heart chamber sensed event signal in response thereto for the duration of a left heart chamber blanking period in response to the generation of a right heart pacing pulse and a left heart pacing pulse.

15. The pacing method of claim 9, further comprising the steps of:

preventing the sensing of spontaneous and evoked cardiac depolarizations in the right heart chamber and the provision of a right heart chamber sensed event signal in response thereto for the duration of a right heart chamber blanking period in response to the generation of a right heart pacing pulse and a left heart pacing pulse; and preventing the sensing of spontaneous and evoked cardiac depolarizations in the left heart chamber and the provision of a left heart chamber sensed event signal in response thereto for the duration of a left heart chamber blanking period in response to the generation of a right heart pacing pulse and a left heart pacing pulse.

16. The pacing method of claim 9, further comprising the steps of:

programming said left heart chamber conduction delay window in a range of 0–100 msec; and programming said right heart chamber conduction delay window in a range of 0–100 msec.

17. A pacing method for improving the hemodynamic efficiency of a sick heart suffering from conduction delays in conducting spontaneous or evoked depolarizations originating in a right heart chamber to the corresponding left heart chamber comprising the steps of:

locating first and second right heart chamber pace/sense electrode in relation with the right heart chamber;

locating first and second left heart chamber pace/sense electrodes in relation with the left heart chamber;

sensing spontaneous and evoked cardiac depolarizations in the right heart chamber across said right heart chamber pace/sense electrodes and providing a right heart chamber sensed event signal;

sensing spontaneous and evoked cardiac depolarizations in the left heart chamber across said left heart chamber pace/sense electrodes and providing a left heart chamber sensed event signal;

timing an escape interval establishing a pacing rate and providing an escape interval pace trigger signal at the time out of the escape interval;

restarting the timing of the escape interval in response to the right heart chamber sensed event signals;

in response to the escape interval pace trigger signal, triggering the right heart pacing pulse output means coupled with said right heart chamber pace/sense electrodes to generate and deliver a right heart pacing pulse to said right heart chamber pace/sense electrodes to evoke a right heart chamber depolarization;

timing a left heart chamber conduction delay window from a right heart chamber sensed event signal or from generation of a right heart pacing pulse and providing a left heart chamber pace trigger signal at the expiration of the left heart chamber conduction delay window;

terminating the timing out of the left heart chamber conduction delay window in response to a left heart chamber sensed event signal; and applying said left heart chamber pace trigger signal to said left heart pacing pulse output means to trigger the generation and delivery of a left heart pacing pulse to said left heart chamber lead means;

whereby an excessive conduction delay between a spontaneous or evoked depolarization in the right heart chamber and the conducted depolarization wave in the left heart chamber is corrected by generation and delivery of a pacing pulse at the timing out of the conduction delay window.

18. The pacing method of claim 17, further comprising the step of:

programming said left heart chamber conduction delay window in a range of 0–100 msec.

19. The pacing method of claim 17, further comprising the steps of:

preventing the sensing of spontaneous and evoked cardiac depolarizations in the right heart chamber and the provision of a right heart chamber sensed event signal in response thereto for the duration of a right heart chamber blanking period in response to the generation of a right heart pacing pulse and a left heart pacing pulse; and preventing the sensing of spontaneous and evoked cardiac depolarizations in the left heart chamber and the provision of a left heart chamber sensed event signal in response thereto for the duration of a left heart chamber blanking period in response to the generation of a right heart pacing pulse and a left heart pacing pulse.

20. A pacing system for improving the hemodynamic efficiency of a sick heart suffering from conduction delays in conducting spontaneous or evoked depolarizations originating in a right heart chamber to the corresponding left heart chamber comprising:

right heart lead means for locating first and second right heart chamber pace/sense electrode in relation with the right heart chamber;

left heart lead means for locating first and second left heart chamber pace/sense electrodes in relation with the left heart chamber;

right heart sensing means for sensing spontaneous and evoked cardiac depolarizations in the right heart chamber across said right heart chamber pace/sense electrodes and providing a right heart chamber sensed event signal;

left heart sensing means for sensing spontaneous and evoked cardiac depolarizations in the left heart chamber across said left heart chamber pace/sense electrodes and providing a left heart chamber sensed event signal;

escape interval timing means for timing an escape interval establishing a pacing rate and providing an escape interval pace trigger signal at the time out of the escape interval;

reset means for restarting the timing of the escape interval in response to the right heart chamber sensed event signals;

right heart chamber pacing pulse output means coupled with said right heart chamber pace/sense electrodes responsive to the escape interval pace trigger signal for generating and delivering a right heart pacing pulse to said right heart chamber pace/sense electrodes to evoke a right heart chamber depolarization;

means for timing a left heart chamber conduction delay window from a right heart chamber sensed event signal or from generation of a right heart pacing pulse and providing a left heart chamber pace trigger signal at the expiration of the left heart chamber conduction delay window;

means for terminating the timing out of the left heart chamber conduction delay window in response to a left heart chamber sensed event signal; and left heart chamber pacing pulse output means coupled with said left heart chamber pace/sense electrodes and responsive to said left heart chamber pace trigger signal for generating and delivering a left heart pacing pulse to said left heart chamber lead means;

whereby an excessive conduction delay between a spontaneous or evoked depolarization in the right heart chamber and the conducted depolarization wave in the left heart chamber is corrected by generation and delivery of a pacing pulse at the timing out of the conduction delay window.

21. The pacing system of claim 20, further comprising:

means for preventing the sensing of spontaneous and evoked cardiac depolarizations in the right heart chamber and the provision of a right heart chamber sensed event signal in response thereto for the duration of a right heart chamber blanking period in response to the generation of a right heart pacing pulse and a left heart pacing pulse; and means for preventing the sensing of spontaneous and evoked cardiac depolarizations in the left heart chamber and the provision of a left heart chamber sensed event signal in response thereto for the duration of a left heart chamber blanking period in response to the generation of a right heart pacing pulse and a left heart pacing pulse.

22. The pacing system of claim 20, further comprising means for programming said left heart chamber conduction delay window in a range of 0–100 msec.

23. A four channel pacing system for improving the hemodynamic efficiency of a sick heart suffering from conduction delays in conducting spontaneous or evoked depolarizations originating in a right heart chamber to the corresponding left heart chamber comprising:

right atrial heart lead means for locating first and second right atrial pace/sense electrodes in relation with the right atrium;

right atrial sensing means for sensing spontaneous and evoked cardiac depolarizations in the right atrium across said right atrium pace/sense electrodes and providing a right atrial sensed event signal;

left atrial lead means for locating first and second left atrial pace/sense electrodes in relation with the left atrium;

left atrial sensing means for sensing spontaneous and evoked cardiac depolarizations in the left atrium across said left atrium pace/sense electrodes and providing a left atrial sensed event signal;

right ventricular heart lead means for locating first and second right ventricular pace/sense electrodes in relation with the right ventricle;

right ventricular sensing means for sensing spontaneous and evoked cardiac depolarizations in the right ventricle across said right ventricular pace/sense electrodes and providing a right ventricular sensed event signal;

means for timing a right heart AV delay from a right atrial sensed event signal or a right atrial pacing pulse and providing a ventricular pace trigger signal upon the time out of the right heart AV delay;

reset means for terminating the timing of the right heart AV delay in response to a right ventricular sensed event signal;

right ventricular pacing pulse output means coupled with said right ventricular pace/sense electrodes responsive to the time out of the right heart AV delay for generating and delivering a right ventricular pacing pulse to said right ventricular pace/sense electrodes to evoke a right ventricular depolarization;

escape interval timing means for timing an escape interval establishing a pacing rate upon the generation of a right ventricular pacing pulse or a right ventricular sensed event signal and providing an escape interval pace trigger signal at the time out of the escape interval;

right atrial pacing pulse output means coupled with said right atrial pace/sense electrodes responsive to the escape interval pace trigger signal for generating and delivering a right atrial pacing pulse to said right atrial pace/sense electrodes to evoke a right atrial depolarization;

means for timing a left atrial conduction delay window from a right atrial sensed event signal or from generation of a right atrial pacing pulse and providing a left atrial pace trigger signal at the expiration of the left atrial conduction delay window;

means for terminating the timing out of the left atrial conduction delay window in response to a left atrial sensed event signal; and left atrial pacing pulse output means coupled with said left atrial pace/sense electrodes and responsive to said left atrial pace trigger signal for generating and delivering a left atrial pacing pulse to said left atrial lead means;

whereby an excessive conduction delay between a spontaneous or evoked depolarization in the right atrium and the conducted depolarization wave in the left atrium is corrected by generation and delivery of a left atrial pacing pulse at the timing out of the left atrial conduction delay window.

24. The four channel pacing system of claim 23, further comprising means for programming said left atrial conduction delay window in a range of 0–100 msec.

25. The four channel pacing system of claim 23, further comprising:

right atrial blanking means for preventing the sensing of spontaneous and evoked cardiac depolarizations in the right atrium and the provision of a right atrial sensed event signal in response thereto for the duration of a right atrial blanking period in response to the generation of right and left atrial pacing pulses and a ventricular pacing pulse; and left atrial blanking means for preventing the sensing of spontaneous and evoked cardiac depolarizations in the left atrium and the provision of a left atrial sensed event signal in response thereto for the duration of a left atrial blanking period in response to the generation of right and left atrial pacing pulses and a ventricular pacing pulse.

26. The four channel pacing system of claim 23, wherein said means for timing a right heart AV delay from a right atrial sensed event signal or a right atrial pacing pulse and providing a ventricular pace trigger signal upon the time out of the right heart AV delay further comprises means for timing a right heart sensed AV delay from a left atrial sensed event signal or a right heart paced AV delay from a right atrial pacing pulse and providing a ventricular pace trigger signal upon the time out of the either the right heart sensed or paced AV delay.

27. The four channel pacing system of claim 23, wherein said means for timing a right heart AV delay from a right atrial sensed event signal or a right atrial pacing pulse and providing a ventricular pace trigger signal upon the time out of the right heart AV delay further comprises means for timing a left heart AV delay from a left atrial sensed event signal or a left atrial pacing pulse and providing a ventricular pace trigger signal upon the time out of the left heart AV delay.

28. The four channel pacing system of claim 27, wherein said means for timing a left heart AV delay from a left atrial sensed event signal or a left atrial pacing pulse further comprises means for timing a left heart sensed AV delay from a left atrial sensed event signal or a left heart paced AV delay from a left atrial pacing pulse and providing a ventricular pace trigger signal upon the time out of the either the left heart sensed or paced AV delay.

29. The four channel pacing system of claim 23, further comprising:

left ventricular lead means for locating first and second left ventricular pace/sense electrodes in relation with the left ventricle;

left ventricular sensing means for sensing spontaneous and evoked cardiac depolarizations in the left ventricle across said left ventricular pace/sense electrodes and providing a left ventricular sensed event signal;

means for timing a left conduction delay window from a right ventricular sensed event signal or from generation of a right ventricular pacing pulse and providing a left ventricular pace trigger signal at the expiration of the left ventricular conduction delay window;

means for terminating the timing out of the left ventricular conduction delay window in response to a left ventricular sensed event signal; and left ventricular pacing pulse output means coupled with said left ventricular pace/sense electrodes and responsive to said left ventricular pace trigger signal for generating and delivering a left ventricular pacing pulse to said left ventricular lead means;

whereby an excessive conduction delay between a spontaneous or evoked depolarization in the right ventricle and the conducted depolarization wave in the left ventricle is corrected by generation and delivery of a left ventricular pacing pulse at the timing out of the left ventricular conduction delay window.

30. The pacing system of claim 29, further comprising means for programming said left ventricular conduction delay window in a range of 0–100 msec.

31. The four channel pacing system of claim 29, further comprising:

right ventricular blanking means for preventing the sensing of spontaneous and evoked cardiac depolarizations in the right ventricle and the provision of a right ventricular sensed event signal in response thereto for the duration of a right ventricular blanking period in response to the generation of right and left atrial and ventricular pacing pulses; and left ventricular blanking means for preventing the sensing of spontaneous and evoked cardiac depolarizations in the left ventricle and the provision of a left ventricular sensed event signal in response thereto for the duration of a left ventricular blanking period in response to the generation of right and left atrial and ventricular pacing pulses.

32. The pacing system of claim 29, further comprising means for programming said left ventricular conduction delay window in a range of 0–100 msec.

* * * * *